(12) United States Patent
Hippe et al.

(10) Patent No.: US 9,173,784 B2
(45) Date of Patent: Nov. 3, 2015

(54) DISPOSABLE DIAPER HAVING REDUCED ABSORBENT CORE TO BACKSHEET GLUING

(71) Applicant: The Procter & Gamble Company, Cincinnati, OH (US)

(72) Inventors: Matthias Konrad Hippe, Sulzbach (DE); Bruno Johannes Ehrnsperger, Bad Soden (DE); Egon Loeffler, Usingen (DE); Ernesto G. Bianchi, Oberursel (DE); Carsten Heinrich Kreuzer, Hofheim (DE); Blanca Arizti, Frankfurt (DE)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 14/485,836

(22) Filed: Sep. 15, 2014

(65) Prior Publication Data
US 2015/0005726 A1 Jan. 1, 2015

Related U.S. Application Data

(63) Continuation of application No. 13/491,987, filed on Jun. 8, 2012.

(30) Foreign Application Priority Data

Jun. 10, 2011 (EP) .................................... 11169528

(51) Int. Cl.
  *A61F 13/15* (2006.01)
  *A61F 13/539* (2006.01)
  (Continued)

(52) U.S. Cl.
  CPC ............... *A61F 13/539* (2013.01); *A61F 13/42* (2013.01); *A61F 13/514* (2013.01); *A61F 13/51498* (2013.01); *A61F 13/53* (2013.01); *A61F 13/536* (2013.01); *A61F 13/5323* (2013.01);
  (Continued)

(58) Field of Classification Search
  CPC ..... A61F 13/53; A61F 13/539; A61F 13/537; A61F 2013/53925; A61F 2013/53778; A61F 2013/530868; A61F 2013/530445
  USPC .......... 604/374, 375, 378, 379, 380, 385.101, 604/385.01, 385.31
  See application file for complete search history.

(56) References Cited

U.S. PATENT DOCUMENTS 1,733,997 A  10/1929  Marr
1,734,499 A  11/1929  Marinsky
(Continued)

FOREIGN PATENT DOCUMENTS

CA  2001370  4/1990
CA  2291997  6/2000
(Continued)

OTHER PUBLICATIONS

International Search Report, PCT/US2012/040714, mailed Aug. 8, 2012, 13 pages.

*Primary Examiner* — Jacqueline Stephens
(74) *Attorney, Agent, or Firm* — Kelly L. McDow

(57) ABSTRACT

The present disclosure generally relates to disposable diapers having absorbent cores comprising superabsorbent polymer particles which are immobilized by adhesive. The absorbent cores are attached to the backsheets of the disposable diapers in certain attachment zones to reduce see-through and the formation of tension lines on the backsheets.

17 Claims, 6 Drawing Sheets

(51) Int. Cl.
  *A61F 13/514* (2006.01)
  *A61F 13/532* (2006.01)
  *A61F 13/536* (2006.01)
  *A61F 13/42* (2006.01)
  *A61F 13/53* (2006.01)

(52) U.S. Cl.
  CPC . *A61F2013/428* (2013.01); *A61F 2013/53051* (2013.01); *A61F 2013/53062* (2013.01); *A61F 2013/530496* (2013.01); *A61F 2013/530554* (2013.01); *A61F 2013/530868* (2013.01); *A61F 2013/53908* (2013.01); *A61F 2013/53925* (2013.01)

(56) References Cited

U.S. PATENT DOCUMENTS

| | | |
|---|---|---|
| 1,989,283 A | 1/1935 | Limacher |
| 2,058,509 A | 10/1936 | Rose |
| 2,271,676 A | 2/1942 | Bjornbak |
| 2,450,789 A | 10/1948 | Frieman |
| 2,508,811 A | 5/1950 | Best et al. |
| 2,568,910 A | 9/1951 | Condylis |
| 2,570,796 A | 10/1951 | Gross |
| 2,570,963 A | 10/1951 | Mesmer |
| 2,583,553 A | 1/1952 | Faure |
| 2,705,957 A | 4/1955 | Mauro |
| 2,788,003 A | 4/1957 | Norden Morin George Van |
| 2,788,786 A | 4/1957 | Dexter |
| 2,798,489 A | 7/1957 | Behrman |
| 2,807,263 A | 9/1957 | Newton |
| 2,830,589 A | 4/1958 | Doner |
| 2,890,700 A | 6/1959 | Lönberg-Holm |
| 2,890,701 A | 6/1959 | Weinman |
| 2,898,912 A | 8/1959 | Adams |
| 2,931,361 A | 4/1960 | Sostsrin |
| 2,977,957 A | 4/1961 | Clyne |
| 3,071,138 A | 1/1963 | Gustavo |
| 3,180,335 A | 4/1965 | Duncan et al. |
| 3,207,158 A | 9/1965 | Yoshitake et al. |
| 3,227,160 A | 1/1966 | Joy |
| 3,386,442 A | 6/1968 | Sabee |
| 3,561,446 A | 2/1971 | Jones |
| 3,572,342 A | 3/1971 | Lindquist et al. |
| 3,572,432 A | 3/1971 | Burton |
| 3,575,174 A | 4/1971 | Mogor |
| 3,578,155 A | 5/1971 | Small et al. |
| 3,606,887 A | 9/1971 | Roeder |
| 3,610,244 A | 10/1971 | Jones |
| 3,618,608 A | 11/1971 | Brink |
| 3,642,001 A | 2/1972 | Sabee |
| 3,653,381 A | 4/1972 | Warnken |
| 3,670,731 A | 6/1972 | Harmon |
| 3,688,767 A | 9/1972 | Goldstein |
| 3,710,797 A | 1/1973 | Marsan |
| 3,731,688 A | 5/1973 | Litt et al. |
| 3,756,878 A | 9/1973 | Willot |
| 3,774,241 A | 11/1973 | Zerkle |
| 3,776,233 A | 12/1973 | Schaar |
| 3,814,100 A | 6/1974 | Nystrand et al. |
| 3,828,784 A | 8/1974 | Zoephel |
| 3,840,418 A | 10/1974 | Sabee |
| 3,847,702 A | 11/1974 | Jones |
| 3,848,594 A | 11/1974 | Buell |
| 3,848,595 A | 11/1974 | Endres |
| 3,848,597 A | 11/1974 | Endres |
| 3,860,003 A | 1/1975 | Buell |
| 3,863,637 A | 2/1975 | MacDonald et al. |
| 3,882,870 A | 5/1975 | Hathaway |
| 3,884,234 A | 5/1975 | Taylor |
| 3,900,032 A | 8/1975 | Heurlen |
| 3,911,173 A | 10/1975 | Sprague, Jr. |
| 3,920,017 A | 11/1975 | Karami |
| 3,924,626 A | 12/1975 | Lee et al. |
| 3,926,189 A | 12/1975 | Taylor |
| 3,929,134 A | 12/1975 | Karami |
| 3,929,135 A | 12/1975 | Thompson |
| 3,930,501 A | 1/1976 | Schaar |
| 3,938,523 A | 2/1976 | Gilliland et al. |
| 3,968,799 A | 7/1976 | Schrading |
| 3,978,861 A | 9/1976 | Schaar |
| 3,981,306 A | 9/1976 | Krusko |
| 3,987,794 A | 10/1976 | Schaar |
| 3,995,637 A | 12/1976 | Schaar |
| 3,995,640 A | 12/1976 | Schaar |
| 3,999,547 A | 12/1976 | Hernandez |
| 4,014,338 A | 3/1977 | Schaar |
| 4,034,760 A | 7/1977 | Amirsakis |
| 4,055,180 A | 10/1977 | Karami |
| 4,074,508 A | 2/1978 | Reid |
| 4,079,739 A | 3/1978 | Whitehead |
| 4,084,592 A | 4/1978 | Tritsch |
| 4,100,922 A | 7/1978 | Hernandez |
| 4,232,674 A | 11/1980 | Melican |
| 4,257,418 A | 3/1981 | Hessner |
| 4,259,220 A | 3/1981 | Bunnelle et al. |
| 4,296,750 A | 10/1981 | Woon et al. |
| 4,315,508 A | 2/1982 | Bolick |
| 4,324,246 A | 4/1982 | Mullane et al. |
| 4,340,706 A | 7/1982 | Obayashi et al. |
| 4,341,216 A | 7/1982 | Obenour |
| 4,342,314 A | 8/1982 | Radel et al. |
| 4,360,021 A | 11/1982 | Stima |
| 4,381,783 A | 5/1983 | Elias |
| 4,388,075 A | 6/1983 | Mesek et al. |
| 4,410,571 A | 10/1983 | Korpman |
| 4,461,621 A | 7/1984 | Karami et al. |
| 4,463,045 A | 7/1984 | Ahr et al. |
| 4,469,710 A | 9/1984 | Rielley et al. |
| 4,475,912 A | 10/1984 | Coates |
| 4,490,148 A | 12/1984 | Beckeström |
| 4,507,438 A | 3/1985 | Obayashi et al. |
| 4,515,595 A | 5/1985 | Kievit et al. |
| 4,527,990 A | 7/1985 | Sigl |
| 4,541,871 A | 9/1985 | Obayashi et al. |
| 4,551,191 A | 11/1985 | Kock et al. |
| 4,573,986 A | 3/1986 | Minetola et al. |
| 4,578,072 A | 3/1986 | Lancaster |
| 4,578,702 A | 3/1986 | Campbell |
| 4,585,448 A | 4/1986 | Enloe |
| 4,585,450 A | 4/1986 | Rosch et al. |
| 4,589,878 A | 5/1986 | Mitrani |
| 4,596,568 A | 6/1986 | Flug |
| 4,601,717 A | 7/1986 | Blevins |
| 4,606,964 A | 8/1986 | Wideman |
| 4,609,518 A | 9/1986 | Curro et al. |
| 4,610,678 A | 9/1986 | Weisman et al. |
| 4,623,342 A | 11/1986 | Ito et al. |
| 4,624,666 A | 11/1986 | Derossett |
| 4,629,643 A | 12/1986 | Curro et al. |
| 4,636,207 A | 1/1987 | Buell |
| 4,641,381 A | 2/1987 | Heran et al. |
| 4,646,510 A | 3/1987 | McIntyre |
| 4,662,875 A | 5/1987 | Hirotsu et al. |
| 4,666,983 A | 5/1987 | Tsubakimoto et al. |
| 4,670,011 A | 6/1987 | Mesek |
| 4,670,012 A | 6/1987 | Johnson |
| 4,680,030 A | 7/1987 | Coates et al. |
| 4,681,579 A | 7/1987 | Toussant et al. |
| 4,681,581 A | 7/1987 | Coates |
| 4,681,793 A | 7/1987 | Linman et al. |
| 4,690,680 A | 9/1987 | Higgins |
| 4,695,278 A | 9/1987 | Lawson |
| 4,699,622 A | 10/1987 | Toussant et al. |
| 4,704,115 A | 11/1987 | Buell |
| 4,704,116 A | 11/1987 | Enloe |
| 4,710,189 A | 12/1987 | Lash |
| 4,720,321 A | 1/1988 | Smith |
| 4,731,066 A | 3/1988 | Korpman |
| 4,731,070 A | 3/1988 | Koci |
| RE32,649 E | 4/1988 | Brandt et al. |
| 4,741,941 A | 5/1988 | Englebert et al. |
| 4,747,846 A | 5/1988 | Boland et al. |
| 4,753,648 A | 6/1988 | Jackson |

(56) References Cited

U.S. PATENT DOCUMENTS

| | | |
|---|---|---|
| 4,773,905 A | 9/1988 | Molee |
| 4,784,892 A | 11/1988 | Storey et al. |
| 4,785,996 A | 11/1988 | Ziecker et al. |
| 4,787,896 A | 11/1988 | Houghton et al. |
| 4,795,454 A | 1/1989 | Dragoo |
| 4,800,102 A | 1/1989 | Takada |
| 4,802,884 A | 2/1989 | Fröidh et al. |
| 4,806,598 A | 2/1989 | Morman |
| 4,808,176 A | 2/1989 | Kielpikowski |
| 4,808,178 A | 2/1989 | Aziz |
| 4,826,880 A | 5/1989 | Lesniak et al. |
| 4,834,735 A | 5/1989 | Alemany et al. |
| 4,834,740 A | 5/1989 | Suzuki et al. |
| 4,834,742 A | 5/1989 | Wilson et al. |
| 4,838,886 A | 6/1989 | Kent |
| 4,842,666 A | 6/1989 | Werenicz |
| 4,846,815 A | 7/1989 | Scripps |
| 4,846,825 A | 7/1989 | Enloe et al. |
| 4,848,815 A | 7/1989 | Molloy |
| 4,861,652 A | 8/1989 | Lippert et al. |
| 4,869,724 A | 9/1989 | Scripps |
| 4,886,697 A | 12/1989 | Perdelwitz, Jr. et al. |
| 4,888,231 A | 12/1989 | Angstadt |
| 4,892,528 A | 1/1990 | Suzuki et al. |
| 4,892,535 A | 1/1990 | Bjornberg et al. |
| 4,892,536 A | 1/1990 | DesMarais et al. |
| 4,894,060 A | 1/1990 | Nestegard |
| 4,894,277 A | 1/1990 | Akasaki |
| 4,900,317 A | 2/1990 | Buell |
| 4,904,251 A | 2/1990 | Igaue et al. |
| 4,909,802 A | 3/1990 | Ahr et al. |
| 4,909,803 A | 3/1990 | Aziz et al. |
| 4,936,839 A | 6/1990 | Molee |
| 4,940,463 A | 7/1990 | Leathers et al. |
| 4,940,464 A | 7/1990 | Van Gompel et al. |
| 4,946,527 A | 8/1990 | Battrell |
| 4,950,264 A | 8/1990 | Osborn |
| 4,960,477 A | 10/1990 | Mesek |
| 4,963,140 A | 10/1990 | Robertson et al. |
| 4,966,809 A | 10/1990 | Tanaka et al. |
| 4,968,313 A | 11/1990 | Sabee |
| 4,990,147 A | 2/1991 | Freeland |
| 4,994,053 A | 2/1991 | Lang |
| 5,006,394 A | 4/1991 | Baird |
| 5,019,063 A | 5/1991 | Marsan et al. |
| 5,019,072 A | 5/1991 | Polski |
| 5,021,051 A | 6/1991 | Hiuke |
| 5,030,314 A | 7/1991 | Lang |
| 5,032,120 A | 7/1991 | Freeland et al. |
| 5,034,008 A | 7/1991 | Breitkopf |
| 5,037,416 A | 8/1991 | Allen et al. |
| 5,071,414 A | 12/1991 | Elliott |
| 5,072,687 A | 12/1991 | Mitchell |
| 5,085,654 A | 2/1992 | Buell |
| 5,087,255 A | 2/1992 | Sims et al. |
| 5,092,861 A | 3/1992 | Nomura et al. |
| 5,102,597 A | 4/1992 | Roe et al. |
| 5,114,420 A | 5/1992 | Igaue et al. |
| 5,124,188 A | 6/1992 | Roe et al. |
| 5,135,522 A | 8/1992 | Fahrenkrug et al. |
| 5,137,537 A | 8/1992 | Herron et al. |
| D329,697 S | 9/1992 | Fahrenkrug et al. |
| 5,143,679 A | 9/1992 | Weber et al. |
| 5,147,343 A | 9/1992 | Kellenberger |
| 5,147,345 A | 9/1992 | Young et al. |
| 5,149,334 A | 9/1992 | Roe et al. |
| 5,149,335 A | 9/1992 | Kellenberger et al. |
| 5,151,091 A | 9/1992 | Glaug |
| 5,151,092 A | 9/1992 | Buell et al. |
| 5,156,793 A | 10/1992 | Buell et al. |
| 5,167,653 A | 12/1992 | Igaue et al. |
| 5,167,897 A | 12/1992 | Weber et al. |
| 5,175,046 A | 12/1992 | Nguyen |
| 5,180,622 A | 1/1993 | Berg et al. |
| 5,190,563 A | 3/1993 | Herron et al. |
| 5,190,606 A | 3/1993 | Merkatoris et al. |
| 5,204,997 A | 4/1993 | Suzuki et al. |
| 5,213,817 A | 5/1993 | Pelley |
| 5,221,274 A | 6/1993 | Buell et al. |
| 5,235,515 A | 8/1993 | Ungpiyakul et al. |
| 5,242,436 A | 9/1993 | Weil et al. |
| 5,246,431 A | 9/1993 | Minetola et al. |
| 5,246,432 A | 9/1993 | Suzuki et al. |
| 5,246,433 A | 9/1993 | Hasse et al. |
| 5,248,309 A | 9/1993 | Serbiak et al. |
| 5,260,345 A | 11/1993 | Desmarais et al. |
| 5,269,775 A | 12/1993 | Freeland et al. |
| 5,281,683 A | 1/1994 | Yano et al. |
| H1298 H | 4/1994 | Ahr |
| 5,300,565 A | 4/1994 | Berg et al. |
| 5,312,386 A | 5/1994 | Correa et al. |
| 5,331,059 A | 7/1994 | Engelhardt et al. |
| 5,336,552 A | 8/1994 | Strack et al. |
| 5,348,547 A | 9/1994 | Payne et al. |
| 5,358,500 A | 10/1994 | LaVon et al. |
| 5,366,782 A | 11/1994 | Curro et al. |
| 5,382,610 A | 1/1995 | Harada et al. |
| 5,387,207 A | 2/1995 | Dyer et al. |
| 5,387,208 A | 2/1995 | Ashton et al. |
| 5,387,209 A | 2/1995 | Yamamoto et al. |
| 5,389,095 A | 2/1995 | Suzuki |
| 5,397,316 A | 3/1995 | Lavon et al. |
| 5,397,317 A | 3/1995 | Thomas |
| 5,399,175 A | 3/1995 | Glaug |
| 5,401,792 A | 3/1995 | Babu et al. |
| 5,409,771 A | 4/1995 | Dahmen et al. |
| H1440 H | 5/1995 | New et al. |
| 5,411,497 A | 5/1995 | Tanzer et al. |
| 5,415,644 A | 5/1995 | Enloe |
| 5,425,725 A | 6/1995 | Tanzer et al. |
| 5,429,630 A | 7/1995 | Beal et al. |
| 5,433,715 A | 7/1995 | Tanzer et al. |
| 5,451,219 A | 9/1995 | Suzuki |
| 5,451,442 A | 9/1995 | Pieniak |
| 5,460,622 A | 10/1995 | Dragoo et al. |
| 5,462,541 A | 10/1995 | Bruemmer et al. |
| 5,476,458 A | 12/1995 | Glaug et al. |
| 5,486,166 A | 1/1996 | Bishop et al. |
| 5,486,167 A | 1/1996 | Dragoo et al. |
| 5,490,846 A | 2/1996 | Ellis et al. |
| 5,492,962 A | 2/1996 | Lahrman et al. |
| 5,494,622 A | 2/1996 | Heath et al. |
| 5,499,978 A | 3/1996 | Buell et al. |
| 5,507,736 A | 4/1996 | Clear et al. |
| 5,507,895 A | 4/1996 | Suekane |
| 5,509,915 A | 4/1996 | Hanson et al. |
| 5,514,104 A | 5/1996 | Cole |
| 5,518,801 A | 5/1996 | Chappell et al. |
| 5,520,674 A | 5/1996 | Hines et al. |
| 5,522,810 A | 6/1996 | Allen, Jr. |
| 5,527,300 A | 6/1996 | Sauer |
| 5,531,730 A | 7/1996 | Dreier |
| 5,532,323 A | 7/1996 | Yano et al. |
| 5,542,943 A | 8/1996 | Sageser |
| 5,549,592 A | 8/1996 | Fries et al. |
| 5,549,593 A | 8/1996 | Ygge et al. |
| 5,549,791 A | 8/1996 | Herron et al. |
| 5,554,145 A | 9/1996 | Roe et al. |
| 5,559,335 A | 9/1996 | Zing et al. |
| 5,560,878 A | 10/1996 | Dragoo et al. |
| 5,562,634 A | 10/1996 | Flumene et al. |
| 5,562,646 A | 10/1996 | Goldman et al. |
| 5,569,234 A | 10/1996 | Buell et al. |
| 5,571,096 A | 11/1996 | Dobrin et al. |
| 5,574,121 A | 11/1996 | Irie et al. |
| 5,580,411 A | 12/1996 | Nease et al. |
| 5,584,829 A | 12/1996 | Lavash et al. |
| 5,586,979 A | 12/1996 | Thomas |
| 5,591,152 A | 1/1997 | Buell et al. |
| 5,591,155 A | 1/1997 | Nishikawa et al. |
| 5,593,399 A | 1/1997 | Tanzer et al. |
| 5,599,335 A | 2/1997 | Goldman et al. |
| 5,601,542 A | 2/1997 | Melius et al. |
| 5,607,414 A | 3/1997 | Richards et al. |

(56) References Cited

U.S. PATENT DOCUMENTS

| | | |
|---|---|---|
| 5,607,416 A | 3/1997 | Yamamoto et al. |
| 5,607,537 A | 3/1997 | Johnson et al. |
| 5,607,760 A | 3/1997 | Roe |
| 5,609,587 A | 3/1997 | Roe |
| 5,609,588 A | 3/1997 | DiPalma et al. |
| 5,611,879 A | 3/1997 | Morman |
| 5,613,959 A | 3/1997 | Roessler et al. |
| 5,613,960 A | 3/1997 | Mizutani |
| 5,614,283 A | 3/1997 | Potnis et al. |
| 5,622,589 A | 4/1997 | Johnson et al. |
| 5,624,423 A | 4/1997 | Anjur |
| 5,624,424 A | 4/1997 | Saisaka et al. |
| 5,625,222 A | 4/1997 | Yoneda et al. |
| 5,626,571 A | 5/1997 | Young et al. |
| 5,628,741 A | 5/1997 | Buell et al. |
| 5,628,845 A | 5/1997 | Murray et al. |
| 5,635,191 A | 6/1997 | Roe et al. |
| 5,635,271 A | 6/1997 | Zafiroglu |
| 5,637,106 A | 6/1997 | Mitchell |
| 5,643,238 A | 7/1997 | Baker |
| 5,643,243 A | 7/1997 | Klemp |
| 5,643,588 A | 7/1997 | Roe et al. |
| 5,649,914 A | 7/1997 | Glaug |
| 5,650,214 A | 7/1997 | Anderson |
| H1674 H | 8/1997 | Ames et al. |
| 5,658,268 A | 8/1997 | Johns et al. |
| 5,662,634 A | 9/1997 | Yamamoto et al. |
| 5,662,638 A | 9/1997 | Johnson et al. |
| 5,662,758 A | 9/1997 | Hamilton et al. |
| 5,669,894 A | 9/1997 | Goldman et al. |
| 5,674,215 A | 10/1997 | Ronnberg |
| 5,683,374 A | 11/1997 | Yamamoto |
| 5,685,874 A | 11/1997 | Buell et al. |
| 5,690,627 A | 11/1997 | Clear et al. |
| 5,691,035 A | 11/1997 | Chappell et al. |
| 5,691,036 A | 11/1997 | Lin et al. |
| 5,695,488 A | 12/1997 | Sosalla |
| 5,700,254 A | 12/1997 | McDowall et al. |
| 5,702,376 A | 12/1997 | Glaug |
| 5,714,156 A | 2/1998 | Schmidt et al. |
| 5,723,087 A | 3/1998 | Chappell et al. |
| 5,733,275 A | 3/1998 | Davis et al. |
| 5,749,866 A | 5/1998 | Roe et al. |
| 5,752,947 A | 5/1998 | Awolin |
| 5,756,039 A | 5/1998 | Mcfall et al. |
| H1732 H | 6/1998 | Johnson |
| 5,762,641 A | 6/1998 | Bewick-Sonntag et al. |
| 5,766,388 A | 6/1998 | Pelley |
| 5,766,389 A | 6/1998 | Brandon et al. |
| 5,772,825 A | 6/1998 | Schmitz |
| 5,776,121 A | 7/1998 | Roe et al. |
| 5,779,831 A | 7/1998 | Schmitz |
| 5,788,684 A | 8/1998 | Abuto et al. |
| 5,795,345 A | 8/1998 | Mizutani |
| 5,797,892 A | 8/1998 | Glaug |
| 5,797,894 A | 8/1998 | Cadieux et al. |
| 5,807,365 A | 9/1998 | Luceri |
| 5,810,796 A | 9/1998 | Kimura et al. |
| 5,810,800 A | 9/1998 | Hunter et al. |
| 5,814,035 A | 9/1998 | Gryskiewicz et al. |
| 5,820,618 A | 10/1998 | Roberts et al. |
| 5,827,257 A | 10/1998 | Fujioka |
| 5,830,202 A | 11/1998 | Bogdanski et al. |
| 5,833,678 A | 11/1998 | Ashton et al. |
| 5,837,789 A | 11/1998 | Stockhausen et al. |
| 5,840,404 A | 11/1998 | Graff |
| 5,843,059 A | 12/1998 | Niemeyer et al. |
| 5,846,231 A | 12/1998 | Fujioka et al. |
| 5,846,232 A | 12/1998 | Serbiak et al. |
| 5,849,816 A | 12/1998 | Suskind et al. |
| 5,851,204 A | 12/1998 | Mizutani |
| 5,855,572 A | 1/1999 | Schmidt |
| 5,858,013 A | 1/1999 | Kling |
| 5,865,823 A | 2/1999 | Curro |
| 5,865,824 A | 2/1999 | Chen |
| 5,873,868 A | 2/1999 | Nakahata |
| 5,876,391 A | 3/1999 | Roe et al. |
| 5,879,751 A | 3/1999 | Bogdanski |
| 5,891,118 A | 4/1999 | Toyoshima |
| 5,891,544 A | 4/1999 | Chappell et al. |
| 5,897,545 A | 4/1999 | Kline et al. |
| 5,904,673 A | 5/1999 | Roe et al. |
| 5,925,439 A | 7/1999 | Haubach |
| 5,928,184 A | 7/1999 | Etheredge |
| 5,931,825 A | 8/1999 | Kuen et al. |
| 5,938,648 A | 8/1999 | Lavon et al. |
| 5,938,650 A | 8/1999 | Baer et al. |
| 5,941,862 A | 8/1999 | Haynes et al. |
| 5,944,706 A | 8/1999 | Palumbo et al. |
| 5,947,949 A | 9/1999 | Inoue et al. |
| 5,951,536 A | 9/1999 | Osborn, III et al. |
| 5,957,908 A | 9/1999 | Kline et al. |
| 5,968,025 A | 10/1999 | Roe et al. |
| 5,968,029 A | 10/1999 | Chappell et al. |
| 5,980,500 A | 11/1999 | Shimizu et al. |
| 5,981,824 A | 11/1999 | Luceri |
| 5,989,236 A | 11/1999 | Roe et al. |
| 6,004,306 A | 12/1999 | Robles et al. |
| 6,022,430 A | 2/2000 | Blenke et al. |
| 6,022,431 A | 2/2000 | Blenke et al. |
| 6,042,673 A | 3/2000 | Johnson et al. |
| 6,050,984 A | 4/2000 | Fujioka |
| 6,054,631 A | 4/2000 | Gent |
| 6,060,115 A | 5/2000 | Borowski et al. |
| 6,068,620 A | 5/2000 | Chmielewski |
| 6,080,909 A | 6/2000 | Osterdahl et al. |
| 6,083,210 A | 7/2000 | Young et al. |
| 6,090,994 A | 7/2000 | Chen |
| 6,091,336 A | 7/2000 | Zand |
| 6,099,515 A | 8/2000 | Sugito |
| 6,102,892 A | 8/2000 | Putzer et al. |
| 6,103,814 A | 8/2000 | Van Drongelen et al. |
| 6,107,537 A | 8/2000 | Elder et al. |
| 6,110,157 A | 8/2000 | Schmidt |
| 6,117,121 A | 9/2000 | Faulks et al. |
| 6,117,803 A | 9/2000 | Morman et al. |
| 6,120,486 A | 9/2000 | Toyoda et al. |
| 6,120,487 A | 9/2000 | Ashton |
| 6,120,489 A | 9/2000 | Johnson et al. |
| 6,120,866 A | 9/2000 | Arakawa et al. |
| 6,121,509 A | 9/2000 | Ashraf et al. |
| 6,129,717 A | 10/2000 | Fujioka et al. |
| 6,129,720 A | 10/2000 | Blenke et al. |
| 6,132,411 A | 10/2000 | Huber et al. |
| 6,139,912 A | 10/2000 | Onuschak |
| 6,143,821 A | 11/2000 | Houben |
| 6,152,908 A | 11/2000 | Widlund |
| 6,156,023 A | 12/2000 | Yoshioka |
| 6,156,424 A | 12/2000 | Taylor |
| 6,160,197 A | 12/2000 | Lassen |
| 6,165,160 A | 12/2000 | Suzuki et al. |
| 6,174,302 B1 | 1/2001 | Kumasaka |
| 6,177,606 B1 | 1/2001 | Etheredge |
| 6,177,607 B1 | 1/2001 | Blaney et al. |
| 6,186,996 B1 | 2/2001 | Martin |
| 6,210,386 B1 | 4/2001 | Inoue |
| 6,210,390 B1 | 4/2001 | Karlsson |
| 6,231,556 B1 | 5/2001 | Osborn, III |
| 6,231,566 B1 | 5/2001 | Lai |
| 6,238,380 B1 | 5/2001 | Sasaki |
| 6,241,716 B1 | 6/2001 | Rönnberg |
| 6,254,294 B1 | 7/2001 | Muhar |
| 6,258,996 B1 | 7/2001 | Goldman |
| 6,265,488 B1 | 7/2001 | Fujino et al. |
| 6,290,686 B1 | 9/2001 | Tanzer et al. |
| 6,306,122 B1 | 10/2001 | Narawa et al. |
| 6,315,765 B1 | 11/2001 | Datta |
| 6,319,239 B1 | 11/2001 | Daniels et al. |
| 6,322,552 B1 | 11/2001 | Blenke et al. |
| 6,325,787 B1 | 12/2001 | Roe et al. |
| 6,326,525 B1 | 12/2001 | Hamajima et al. |
| 6,330,735 B1 | 12/2001 | Hahn et al. |
| 6,334,858 B1 | 1/2002 | Rönnberg et al. |
| 6,336,922 B1 | 1/2002 | Van Gompel et al. |

(56) References Cited

U.S. PATENT DOCUMENTS

| | | |
|---|---|---|
| 6,340,611 B1 | 1/2002 | Shimizu |
| 6,342,715 B1 | 1/2002 | Shimizu |
| 6,350,332 B1 | 2/2002 | Thomas et al. |
| 6,368,687 B1 | 4/2002 | Joseph et al. |
| 6,371,948 B1 | 4/2002 | Mizutani |
| 6,372,952 B1 | 4/2002 | Lash et al. |
| 6,375,644 B2 | 4/2002 | Mizutani |
| 6,376,034 B1 | 4/2002 | Brander |
| 6,383,431 B1 | 5/2002 | Dobrin et al. |
| 6,383,960 B1 | 5/2002 | Everett et al. |
| 6,394,989 B2 | 5/2002 | Mizutani |
| 6,402,729 B1 | 6/2002 | Boberg et al. |
| 6,402,731 B1 | 6/2002 | Suprise et al. |
| 6,403,857 B1 | 6/2002 | Gross et al. |
| 6,409,883 B1 | 6/2002 | Makolin et al. |
| 6,410,820 B1 | 6/2002 | McFall et al. |
| 6,410,822 B1 | 6/2002 | Mizutani |
| 6,413,248 B1 | 7/2002 | Mizutani |
| 6,413,249 B1 | 7/2002 | Turi et al. |
| 6,414,214 B1 | 7/2002 | Engelhardt et al. |
| 6,416,502 B1 | 7/2002 | Connelly et al. |
| 6,416,697 B1 | 7/2002 | Venturino et al. |
| 6,419,667 B1 | 7/2002 | Avalon et al. |
| 6,423,046 B1 | 7/2002 | Fujioka et al. |
| 6,423,048 B1 | 7/2002 | Suzuki et al. |
| 6,423,884 B1 | 7/2002 | Oehmen |
| 6,429,350 B1 | 8/2002 | Tanzer et al. |
| 6,432,094 B1 | 8/2002 | Fujioka et al. |
| 6,432,098 B1 | 8/2002 | Kline et al. |
| 6,432,099 B2 | 8/2002 | Rönnberg |
| 6,437,214 B1 | 8/2002 | Everett et al. |
| 6,441,268 B1 | 8/2002 | Edwardsson |
| 6,443,933 B1 | 9/2002 | Suzuki et al. |
| 6,444,064 B1 | 9/2002 | Henry et al. |
| 6,447,496 B1 | 9/2002 | Mizutani |
| 6,458,111 B1 | 10/2002 | Onishi et al. |
| 6,458,877 B1 | 10/2002 | Ahmed et al. |
| 6,459,016 B1 | 10/2002 | Rosenfeld et al. |
| 6,461,342 B2 | 10/2002 | Tanji et al. |
| 6,461,343 B1 | 10/2002 | Schaefer et al. |
| 6,472,478 B1 | 10/2002 | Funk et al. |
| 6,475,201 B2 | 11/2002 | Saito et al. |
| 6,494,872 B1 | 12/2002 | Suzuki et al. |
| 6,494,873 B2 | 12/2002 | Karlsson et al. |
| 6,500,159 B1 | 12/2002 | Carvalho |
| 6,503,233 B1 | 1/2003 | Chen |
| 6,503,979 B1 | 1/2003 | Funk et al. |
| 6,506,186 B1 | 1/2003 | Roessler |
| 6,506,961 B1 | 1/2003 | Levy |
| 6,515,195 B1 | 2/2003 | Lariviere |
| 6,517,525 B1 | 2/2003 | Berthou |
| 6,518,479 B1 | 2/2003 | Graef |
| 6,520,947 B1 | 2/2003 | Tilly et al. |
| 6,521,811 B1 | 2/2003 | Lassen |
| 6,521,812 B1 | 2/2003 | Graef et al. |
| 6,524,294 B1 | 2/2003 | Hilston et al. |
| 6,525,240 B1 | 2/2003 | Graef |
| 6,528,698 B2 | 3/2003 | Mizutani et al. |
| 6,529,860 B1 | 3/2003 | Strumolo et al. |
| 6,531,025 B1 | 3/2003 | Lender et al. |
| 6,531,027 B1 | 3/2003 | Lender et al. |
| 6,534,149 B1 | 3/2003 | Daley et al. |
| 6,559,081 B1 | 5/2003 | Erspamer |
| 6,559,239 B1 | 5/2003 | Riegel et al. |
| 6,562,168 B1 | 5/2003 | Schmitt et al. |
| 6,562,192 B1 | 5/2003 | Hamilton |
| 6,569,137 B2 | 5/2003 | Suzuki et al. |
| 6,573,422 B1 | 6/2003 | Rosenfeld |
| 6,585,713 B1 | 7/2003 | LeMahieu et al. |
| 6,585,858 B1 | 7/2003 | Otto et al. |
| 6,602,234 B2 | 8/2003 | Klemp et al. |
| 6,605,070 B2 | 8/2003 | Ludwig et al. |
| 6,605,172 B1 | 8/2003 | Anderson et al. |
| 6,605,752 B2 | 8/2003 | Magnusson et al. |
| 6,610,900 B1 | 8/2003 | Tanzer |
| 6,630,054 B1 | 10/2003 | Graef |
| 6,632,209 B1 | 10/2003 | Chmielewski |
| 6,632,504 B1 | 10/2003 | Gillespie et al. |
| 6,645,569 B2 | 11/2003 | Cramer et al. |
| 6,646,180 B1 | 11/2003 | Chmielewski |
| 6,648,869 B1 | 11/2003 | Gillies et al. |
| 6,648,870 B2 | 11/2003 | Itoh et al. |
| 6,648,871 B2 | 11/2003 | Kusibojoska et al. |
| 6,649,807 B2 | 11/2003 | Mizutani |
| 6,649,810 B1 | 11/2003 | Minato et al. |
| 6,657,015 B1 | 12/2003 | Riegel et al. |
| 6,657,102 B2 | 12/2003 | Furuya |
| 6,667,424 B1 | 12/2003 | Hamilton |
| 6,670,522 B1 | 12/2003 | Graef |
| 6,673,982 B1 | 1/2004 | Chen |
| 6,673,983 B1 | 1/2004 | Graef |
| 6,673,985 B2 | 1/2004 | Mizutani |
| 6,682,515 B1 | 1/2004 | Mizutani et al. |
| 6,682,516 B2 | 1/2004 | Johnston |
| 6,689,115 B1 | 2/2004 | Popp et al. |
| 6,689,934 B2 | 2/2004 | Dodge, II et al. |
| 6,695,827 B2 | 2/2004 | Chen |
| 6,700,034 B1 | 3/2004 | Lindsay et al. |
| 6,703,538 B2 | 3/2004 | Lassen |
| 6,705,465 B2 | 3/2004 | Ling et al. |
| 6,706,129 B2 | 3/2004 | Ando et al. |
| 6,706,943 B2 | 3/2004 | Onishi |
| 6,710,224 B2 | 3/2004 | Chmielewski et al. |
| 6,710,225 B1 | 3/2004 | Everett et al. |
| 6,716,205 B2 | 4/2004 | Popp et al. |
| 6,716,441 B1 | 4/2004 | Osborne et al. |
| 6,717,029 B2 | 4/2004 | Baker |
| 6,726,668 B2 | 4/2004 | Underhill et al. |
| 6,726,792 B1 | 4/2004 | Johnson et al. |
| 6,730,387 B2 | 5/2004 | Rezai et al. |
| 6,734,335 B1 | 5/2004 | Graef |
| 6,790,798 B1 | 9/2004 | Suzuki et al. |
| 6,802,834 B2 | 10/2004 | Melius et al. |
| 6,809,158 B2 | 10/2004 | Ikeuchi et al. |
| 6,811,642 B2 | 11/2004 | Ochi |
| 6,818,083 B2 | 11/2004 | Mcamish et al. |
| 6,818,166 B2 | 11/2004 | Edwardson et al. |
| 6,830,800 B2 | 12/2004 | Curro et al. |
| 6,832,905 B2 | 12/2004 | Delzer et al. |
| 6,840,929 B2 | 1/2005 | Kurata |
| 6,846,374 B2 | 1/2005 | Popp |
| 6,858,771 B2 | 2/2005 | Yoshimasa |
| 6,863,933 B2 | 3/2005 | Cramer et al. |
| 6,863,960 B2 | 3/2005 | Curro et al. |
| 6,867,345 B2 | 3/2005 | Shimoe et al. |
| 6,867,346 B1 | 3/2005 | Dopps |
| 6,878,433 B2 | 4/2005 | Curro et al. |
| 6,880,211 B2 | 4/2005 | Jackson et al. |
| 6,891,080 B2 | 5/2005 | Minato |
| 6,904,865 B2 | 6/2005 | Klofta |
| 6,911,574 B1 | 6/2005 | Mizutani |
| 6,923,797 B2 | 8/2005 | Shinohara et al. |
| 6,923,926 B2 | 8/2005 | Walter et al. |
| 6,926,703 B2 | 8/2005 | Sugito |
| 6,929,629 B2 | 8/2005 | Drevik et al. |
| 6,939,914 B2 | 9/2005 | Qin et al. |
| 6,946,585 B2 | 9/2005 | Brown |
| 6,953,451 B2 | 10/2005 | Berba |
| 6,955,733 B2 | 10/2005 | Henry et al. |
| 6,962,578 B1 | 11/2005 | LaVon |
| 6,962,645 B2 | 11/2005 | Graef |
| 6,965,058 B1 | 11/2005 | Raidel |
| 6,969,781 B2 | 11/2005 | Graef |
| 6,972,010 B2 | 12/2005 | Pesce et al. |
| 6,972,011 B2 | 12/2005 | Maeda et al. |
| 6,979,564 B2 | 12/2005 | Glucksmann et al. |
| 6,982,052 B2 | 1/2006 | Daniels et al. |
| 7,001,167 B2 | 2/2006 | Venturino |
| 7,014,632 B2 | 3/2006 | Takino et al. |
| 7,015,370 B2 | 3/2006 | Watanabe |
| 7,037,299 B2 | 5/2006 | Turi et al. |
| 7,037,571 B2 | 5/2006 | Fish et al. |
| 7,048,726 B2 | 5/2006 | Kusagawa et al. |
| 7,056,311 B2 | 6/2006 | Kinoshita |

(56) References Cited

U.S. PATENT DOCUMENTS

| | | |
|---|---|---|
| 7,067,711 B2 | 6/2006 | Kinoshita et al. |
| 7,073,373 B2 | 7/2006 | La Fortune |
| 7,078,583 B2 | 7/2006 | Kudo |
| 7,090,665 B2 | 8/2006 | Ohashi |
| 7,108,759 B2 | 9/2006 | You |
| 7,108,916 B2 | 9/2006 | Ehrnsperger et al. |
| 7,112,621 B2 | 9/2006 | Rohrbaugh et al. |
| 7,122,713 B2 | 10/2006 | Komatsu |
| 7,125,470 B2 | 10/2006 | Graef |
| 7,132,585 B2 | 11/2006 | Kudo |
| 7,147,628 B2 | 12/2006 | Drevik |
| 7,150,729 B2 | 12/2006 | Shimada |
| 7,154,019 B2 | 12/2006 | Mishima et al. |
| 7,160,281 B2 | 1/2007 | Leminh et al. |
| 7,163,528 B2 | 1/2007 | Christon et al. |
| 7,166,190 B2 | 1/2007 | Graef |
| 7,169,136 B2 | 1/2007 | Otsubo |
| 7,183,360 B2 | 2/2007 | Daniel et al. |
| 7,189,888 B2 | 3/2007 | Wang et al. |
| 7,196,241 B2 | 3/2007 | Kinoshita |
| 7,199,211 B2 | 4/2007 | Popp et al. |
| 7,204,830 B2 | 4/2007 | Mishima |
| 7,207,978 B2 | 4/2007 | Takino |
| 7,219,403 B2 | 5/2007 | Miyamoto et al. |
| 7,220,251 B2 | 5/2007 | Otsubo et al. |
| 7,241,280 B2 | 7/2007 | Christen et al. |
| 7,250,481 B2 | 7/2007 | Jaworek et al. |
| 7,252,657 B2 | 8/2007 | Mishima |
| 7,265,258 B2 | 9/2007 | Hamilton |
| 7,270,651 B2 | 9/2007 | Adams et al. |
| 7,285,178 B2 | 10/2007 | Mischler et al. |
| RE39,919 E | 11/2007 | Dodge, II et al. |
| 7,306,582 B2 | 12/2007 | Adams et al. |
| 7,311,696 B2 | 12/2007 | Christen et al. |
| 7,311,968 B2 | 12/2007 | Ehrnsperger et al. |
| 7,312,372 B2 | 12/2007 | Miyama |
| 7,318,820 B2 | 1/2008 | LaVon et al. |
| 7,329,244 B2 | 2/2008 | Otsubo |
| 7,329,246 B2 | 2/2008 | Kinoshita |
| 7,335,810 B2 | 2/2008 | Yoshimasa |
| 7,377,914 B2 | 5/2008 | LaVon |
| 7,429,689 B2 | 9/2008 | Chen |
| 7,435,244 B2 | 10/2008 | Schroer et al. |
| 7,465,373 B2 | 12/2008 | Graef |
| 7,500,969 B2 | 3/2009 | Mishima |
| 7,504,552 B2 | 3/2009 | Tamura |
| 7,521,109 B2 | 4/2009 | Suzuki et al. |
| 7,521,587 B2 | 4/2009 | Busam et al. |
| 7,537,832 B2 | 5/2009 | Carlucci et al. |
| 7,547,815 B2 | 6/2009 | Ohashi |
| 7,550,646 B2 | 6/2009 | Tamura |
| 7,563,257 B2 | 7/2009 | Nakajima |
| 7,588,561 B2 | 9/2009 | Kenmochi |
| 7,594,904 B2 | 9/2009 | Rosenfeld |
| 7,598,428 B2 | 10/2009 | Gustavsson et al. |
| 7,625,363 B2 | 12/2009 | Yoshimasa |
| 7,641,642 B2 | 1/2010 | Murai et al. |
| 7,648,490 B2 | 1/2010 | Kuroda |
| 7,652,111 B2 | 1/2010 | Hermeling et al. |
| 7,666,173 B2 | 2/2010 | Mishima |
| 7,666,174 B2 | 2/2010 | Kawakami et al. |
| 7,686,790 B2 | 3/2010 | Rasmussen et al. |
| 7,687,596 B2 | 3/2010 | Hermeling et al. |
| 7,695,461 B2 | 4/2010 | Rosenfeld |
| 7,696,402 B2 | 4/2010 | Nishikawa |
| 7,708,725 B2 | 5/2010 | Tamagawa |
| 7,717,150 B2 | 5/2010 | Manabe |
| 7,722,587 B2 | 5/2010 | Suzuki et al. |
| 7,722,590 B2 | 5/2010 | Tsuji |
| 7,727,217 B2 | 6/2010 | Hancock-Cooke |
| 7,736,351 B2 | 6/2010 | Nigam |
| 7,737,324 B2 | 6/2010 | LaVon et al. |
| 7,744,576 B2 | 6/2010 | Busam et al. |
| 7,744,578 B2 | 6/2010 | Tanio et al. |
| 7,750,203 B2 | 7/2010 | Busam et al. |
| 7,754,822 B2 | 7/2010 | Daniel et al. |
| 7,754,940 B2 | 7/2010 | Brisebois |
| 7,759,540 B2 | 7/2010 | Litvay et al. |
| 7,763,004 B2 | 7/2010 | Beck |
| 7,767,875 B2 | 8/2010 | Olson |
| 7,767,878 B2 | 8/2010 | Suzuki |
| 7,772,420 B2 | 8/2010 | Hermeling et al. |
| 7,786,341 B2 | 8/2010 | Schneider et al. |
| 7,795,492 B2 | 9/2010 | Vartiainen |
| 7,803,145 B2 | 9/2010 | Rosenfeld |
| 7,825,291 B2 | 11/2010 | Elfsberg et al. |
| 7,838,722 B2 | 11/2010 | Blessing et al. |
| 7,850,672 B2 | 12/2010 | Guidotti et al. |
| 7,851,667 B2 | 12/2010 | Becker et al. |
| 7,855,314 B2 | 12/2010 | Hanao |
| 7,857,797 B2 | 12/2010 | Kudo |
| 7,858,842 B2 | 12/2010 | Komatsu |
| 7,884,259 B2 | 2/2011 | Hanao |
| 7,888,549 B2 | 2/2011 | Jansson et al. |
| 7,910,797 B2 | 3/2011 | Nandrea |
| 7,931,636 B2 | 4/2011 | LaVon et al. |
| 7,935,207 B2 | 5/2011 | Zhao |
| 7,935,861 B2 | 5/2011 | Suzuki |
| 7,938,813 B2 | 5/2011 | Wang et al. |
| 7,942,858 B2 | 5/2011 | Francoeur |
| 7,951,126 B2 | 5/2011 | Nanjyo |
| 7,982,091 B2 | 7/2011 | Konawa |
| 7,993,319 B2 | 8/2011 | Sperl |
| 8,017,827 B2 | 9/2011 | Hundorf et al. |
| 8,029,486 B2 | 10/2011 | Nakajima |
| 8,034,991 B2 | 10/2011 | Bruzadin et al. |
| 8,039,684 B2 | 10/2011 | Guidotti et al. |
| 8,052,454 B2 | 11/2011 | Polnyi |
| 8,057,620 B2 | 11/2011 | Perego et al. |
| 8,109,915 B2 | 2/2012 | Shimoe |
| 8,133,212 B2 | 3/2012 | Takada |
| 8,148,598 B2 | 4/2012 | Tsang et al. |
| 8,163,124 B2 | 4/2012 | Moriura et al. |
| 8,167,862 B2 | 5/2012 | Digiacomantonio et al. |
| 8,173,858 B2 | 5/2012 | Kuroda |
| 8,178,747 B2 | 5/2012 | Venturino et al. |
| 8,183,430 B2 | 5/2012 | Hakansson et al. |
| 8,186,296 B2 | 5/2012 | Brown et al. |
| 8,187,239 B2 | 5/2012 | LaVon et al. |
| 8,187,240 B2 | 5/2012 | Busam et al. |
| 8,198,506 B2 | 6/2012 | Venturino et al. |
| 8,211,815 B2 | 7/2012 | Baker |
| 8,236,715 B2 | 8/2012 | Schmidt et al. |
| 8,237,012 B2 | 8/2012 | Miyama |
| 8,246,594 B2 | 8/2012 | Sperl |
| 8,258,367 B2 | 9/2012 | Lawson et al. |
| 8,268,424 B1 | 9/2012 | Suzuki |
| 8,273,943 B2 | 9/2012 | Noda |
| 8,283,516 B2 | 10/2012 | Litvay |
| 8,317,766 B2 | 11/2012 | Naoto |
| 8,317,768 B2 | 11/2012 | Larsson |
| 8,319,005 B2 | 11/2012 | Becker et al. |
| 8,343,123 B2 | 1/2013 | Noda |
| 8,343,296 B2 | 1/2013 | Blessing et al. |
| 8,360,977 B2 | 1/2013 | Marttila |
| 8,361,047 B2 | 1/2013 | Mukai |
| 8,377,025 B2 | 2/2013 | Nakajima |
| 8,450,555 B2 | 5/2013 | Nhan et al. |
| 8,496,637 B2 | 7/2013 | Hundorf et al. |
| 8,519,213 B2 | 8/2013 | Venturino et al. |
| 8,524,355 B2 | 9/2013 | Nakaoka |
| 8,552,252 B2 | 10/2013 | Hundorf et al. |
| 8,568,566 B2 | 10/2013 | Jackels et al. |
| 8,581,019 B2 | 11/2013 | Carlucci et al. |
| 8,603,058 B2 | 12/2013 | Sperl et al. |
| 8,604,270 B2 | 12/2013 | Venturino et al. |
| 8,633,347 B2 | 1/2014 | Bianco et al. |
| 8,664,468 B2 | 3/2014 | Lawson et al. |
| 8,674,170 B2 | 3/2014 | Busam et al. |
| 8,734,417 B2 | 5/2014 | LaVon et al. |
| 8,766,031 B2 | 7/2014 | Becker et al. |
| 8,772,570 B2 | 7/2014 | Kawakami et al. |
| 8,784,594 B2 | 7/2014 | Blessing et al. |
| 8,785,715 B2 | 7/2014 | Wright et al. |

(56) References Cited

U.S. PATENT DOCUMENTS

| | | |
|---|---|---|
| 8,791,318 B2 | 7/2014 | Becker et al. |
| 2001/0007065 A1 | 7/2001 | Blanchard |
| 2001/0008964 A1 | 7/2001 | Kurata et al. |
| 2001/0016548 A1 | 8/2001 | Kugler et al. |
| 2001/0020157 A1 | 9/2001 | Mizutani |
| 2001/0037101 A1 | 11/2001 | Allan et al. |
| 2001/0044610 A1 | 11/2001 | Kim |
| 2002/0007167 A1 | 1/2002 | Dan |
| 2002/0007169 A1 | 1/2002 | Graef et al. |
| 2002/0016122 A1 | 2/2002 | Curro et al. |
| 2002/0016579 A1 | 2/2002 | Stenberg |
| 2002/0045881 A1 | 4/2002 | Kusibojoska et al. |
| 2002/0056516 A1 | 5/2002 | Ochi |
| 2002/0058919 A1 | 5/2002 | Hamilton et al. |
| 2002/0062112 A1 | 5/2002 | Mizutani |
| 2002/0062115 A1 | 5/2002 | Wada et al. |
| 2002/0062116 A1 | 5/2002 | Mizutani et al. |
| 2002/0065498 A1 | 5/2002 | Ohashi |
| 2002/0072471 A1 | 6/2002 | Ikeuchi et al. |
| 2002/0082575 A1 | 6/2002 | Dan |
| 2002/0087139 A1 | 7/2002 | Popp et al. |
| 2002/0095127 A1 | 7/2002 | Fish et al. |
| 2002/0102392 A1 | 8/2002 | Fish et al. |
| 2002/0115969 A1 | 8/2002 | Maeda et al. |
| 2002/0123728 A1 | 9/2002 | Graef et al. |
| 2002/0123848 A1 | 9/2002 | Schneiderman et al. |
| 2002/0151634 A1 | 10/2002 | Rohrbaugh et al. |
| 2002/0151861 A1 | 10/2002 | Klemp et al. |
| 2002/0173767 A1 | 11/2002 | Popp et al. |
| 2002/0192366 A1 | 12/2002 | Cramer et al. |
| 2002/0197695 A1 | 12/2002 | Glucksmann et al. |
| 2003/0036741 A1 | 2/2003 | Abba et al. |
| 2003/0078553 A1 | 4/2003 | Wada |
| 2003/0084983 A1 | 5/2003 | Rangachari et al. |
| 2003/0088223 A1 | 5/2003 | Vogt et al. |
| 2003/0105190 A1 | 6/2003 | Diehl et al. |
| 2003/0109839 A1 | 6/2003 | Costea et al. |
| 2003/0114811 A1 | 6/2003 | Christen et al. |
| 2003/0114816 A1 | 6/2003 | Underhill |
| 2003/0114818 A1 | 6/2003 | Benecke et al. |
| 2003/0115969 A1 | 6/2003 | Koyano et al. |
| 2003/0120235 A1 | 6/2003 | Boulanger |
| 2003/0120249 A1 | 6/2003 | Wulz et al. |
| 2003/0135176 A1 | 7/2003 | Delzer et al. |
| 2003/0135181 A1 | 7/2003 | Chen et al. |
| 2003/0135182 A1 | 7/2003 | Woon et al. |
| 2003/0139712 A1 | 7/2003 | Dodge |
| 2003/0139715 A1 | 7/2003 | Dodge |
| 2003/0139718 A1 | 7/2003 | Graef |
| 2003/0144642 A1 | 7/2003 | Dopps |
| 2003/0144644 A1 | 7/2003 | Murai et al. |
| 2003/0148684 A1 | 8/2003 | Cramer et al. |
| 2003/0148694 A1 | 8/2003 | Ghiam |
| 2003/0158531 A1 | 8/2003 | Chmielewski |
| 2003/0167045 A1 | 9/2003 | Graef |
| 2003/0171727 A1 | 9/2003 | Graef |
| 2003/0208175 A1 | 11/2003 | Gross |
| 2003/0225385 A1 | 12/2003 | Glaug |
| 2003/0233082 A1 | 12/2003 | Kline et al. |
| 2003/0236512 A1 | 12/2003 | Baker |
| 2004/0019338 A1 | 1/2004 | Litvay et al. |
| 2004/0022998 A1 | 2/2004 | Miyamoto et al. |
| 2004/0033750 A1 | 2/2004 | Everett |
| 2004/0063367 A1 | 4/2004 | Dodge |
| 2004/0064115 A1 | 4/2004 | Arora |
| 2004/0064116 A1 | 4/2004 | Arora |
| 2004/0064125 A1 | 4/2004 | Justmann et al. |
| 2004/0065420 A1 | 4/2004 | Graef |
| 2004/0082928 A1 | 4/2004 | Pesce et al. |
| 2004/0097895 A1 | 5/2004 | Busam et al. |
| 2004/0122411 A1 | 6/2004 | Hancock-Cooke |
| 2004/0127131 A1 | 7/2004 | Potnis |
| 2004/0127871 A1 | 7/2004 | Odorzynski |
| 2004/0127872 A1 | 7/2004 | Petryk |
| 2004/0134596 A1 | 7/2004 | Rosati et al. |
| 2004/0138633 A1 | 7/2004 | Mishima et al. |
| 2004/0147890 A1 | 7/2004 | Nakahata et al. |
| 2004/0158212 A1 | 8/2004 | Ponomarenko et al. |
| 2004/0162536 A1 | 8/2004 | Becker et al. |
| 2004/0167486 A1 | 8/2004 | Busam et al. |
| 2004/0167489 A1 | 8/2004 | Kellenberger et al. |
| 2004/0170813 A1 | 9/2004 | Digiacomantonio et al. |
| 2004/0193127 A1 | 9/2004 | Hansson |
| 2004/0215160 A1 | 10/2004 | Chmielewski |
| 2004/0220541 A1 | 11/2004 | Suzuki et al. |
| 2004/0225271 A1 | 11/2004 | Datta et al. |
| 2004/0231065 A1 | 11/2004 | Daniel et al. |
| 2004/0236299 A1 | 11/2004 | Tsang et al. |
| 2004/0236455 A1 | 11/2004 | Woltman et al. |
| 2004/0249355 A1 | 12/2004 | Tanio et al. |
| 2004/0260259 A1 | 12/2004 | Baker |
| 2005/0004543 A1 | 1/2005 | Schroer et al. |
| 2005/0004548 A1 | 1/2005 | Otsubo et al. |
| 2005/0008839 A1 | 1/2005 | Cramer et al. |
| 2005/0018258 A1 | 1/2005 | Miyagi |
| 2005/0038401 A1 | 2/2005 | Suzuki et al. |
| 2005/0070867 A1 | 3/2005 | Beruda et al. |
| 2005/0085784 A1 | 4/2005 | LeMinh et al. |
| 2005/0090789 A1 | 4/2005 | Graef |
| 2005/0101929 A1 | 5/2005 | Waksmundzki et al. |
| 2005/0137543 A1 | 6/2005 | Underhill et al. |
| 2005/0148258 A1 | 7/2005 | Chakravarty |
| 2005/0148990 A1 | 7/2005 | Shimoe |
| 2005/0154363 A1 | 7/2005 | Minato |
| 2005/0159720 A1 | 7/2005 | Gentilcore |
| 2005/0165208 A1 | 7/2005 | Popp et al. |
| 2005/0171499 A1 | 8/2005 | Nigam et al. |
| 2005/0176910 A1 | 8/2005 | Jaworek et al. |
| 2005/0203475 A1 | 9/2005 | LaVon et al. |
| 2005/0215752 A1 | 9/2005 | Popp et al. |
| 2005/0229543 A1 | 10/2005 | Tippey |
| 2005/0245684 A1 | 11/2005 | Daniel et al. |
| 2005/0288645 A1 | 12/2005 | LaVon |
| 2005/0288646 A1 | 12/2005 | LaVon |
| 2006/0004334 A1 | 1/2006 | Schlinz et al. |
| 2006/0021695 A1 | 2/2006 | Blessing et al. |
| 2006/0024433 A1 | 2/2006 | Blessing et al. |
| 2006/0069367 A1 | 3/2006 | Waksmundzki et al. |
| 2006/0069371 A1 | 3/2006 | Ohashi et al. |
| 2006/0073969 A1 | 4/2006 | Torli et al. |
| 2006/0081348 A1 | 4/2006 | Graef |
| 2006/0129114 A1 | 6/2006 | Mason et al. |
| 2006/0142724 A1 | 6/2006 | Watanabe |
| 2006/0155057 A1 | 7/2006 | Hermeling et al. |
| 2006/0155254 A1 | 7/2006 | Sanz et al. |
| 2006/0167215 A1 | 7/2006 | Hermeling et al. |
| 2006/0177647 A1 | 8/2006 | Schmidt et al. |
| 2006/0178071 A1 | 8/2006 | Schmidt et al. |
| 2006/0184146 A1 | 8/2006 | Suzuki |
| 2006/0184149 A1 | 8/2006 | Kasai et al. |
| 2006/0189954 A1 | 8/2006 | Kudo |
| 2006/0202380 A1 | 9/2006 | Bentley |
| 2006/0206091 A1 | 9/2006 | Cole |
| 2006/0211828 A1 | 9/2006 | Daniel et al. |
| 2006/0240229 A1 | 10/2006 | Ehrnsperger et al. |
| 2006/0264860 A1 | 11/2006 | Beck |
| 2006/0264861 A1 | 11/2006 | Lavon et al. |
| 2006/0271010 A1 | 11/2006 | LaVon et al. |
| 2007/0027436 A1 | 2/2007 | Nakagawa et al. |
| 2007/0032770 A1 | 2/2007 | Lavon et al. |
| 2007/0043191 A1 | 2/2007 | Hermeling et al. |
| 2007/0043330 A1 | 2/2007 | Lankhof et al. |
| 2007/0049892 A1 | 3/2007 | Lord et al. |
| 2007/0049897 A1 | 3/2007 | LaVon et al. |
| 2007/0073253 A1 | 3/2007 | Miyama |
| 2007/0078422 A1 | 4/2007 | Glaug |
| 2007/0088308 A1 | 4/2007 | Ehrnsperger et al. |
| 2007/0093164 A1 | 4/2007 | Nakaoka |
| 2007/0093767 A1 | 4/2007 | Carlucci et al. |
| 2007/0100307 A1 | 5/2007 | Nomoto |
| 2007/0118087 A1 | 5/2007 | Flohr et al. |
| 2007/0123834 A1 | 5/2007 | McDowall et al. |
| 2007/0156108 A1 | 7/2007 | Becker et al. |
| 2007/0156110 A1 | 7/2007 | Thyfault |

(56) References Cited

U.S. PATENT DOCUMENTS

| | | |
|---|---|---|
| 2007/0167928 A1 | 7/2007 | Becker et al. |
| 2007/0179464 A1 | 8/2007 | Becker et al. |
| 2007/0179469 A1 | 8/2007 | Takahashi et al. |
| 2007/0191798 A1 | 8/2007 | Glaug |
| 2007/0219521 A1 | 9/2007 | Hird et al. |
| 2007/0219523 A1 | 9/2007 | Bruun |
| 2007/0244455 A1 | 10/2007 | Hansson et al. |
| 2007/0246147 A1 | 10/2007 | Venturino et al. |
| 2007/0282288 A1 | 12/2007 | Noda |
| 2007/0282290 A1 | 12/2007 | Cole |
| 2007/0282291 A1 | 12/2007 | Cole |
| 2008/0027402 A1 | 1/2008 | Schmidt et al. |
| 2008/0032035 A1 | 2/2008 | Schmidt et al. |
| 2008/0091159 A1 | 4/2008 | Carlucci et al. |
| 2008/0119810 A1 | 5/2008 | Kuroda |
| 2008/0125735 A1 | 5/2008 | Busam et al. |
| 2008/0132864 A1 | 6/2008 | Lawson et al. |
| 2008/0221538 A1 | 9/2008 | Zhao |
| 2008/0221539 A1 | 9/2008 | Zhao |
| 2008/0228158 A1 | 9/2008 | Sue et al. |
| 2008/0262459 A1 | 10/2008 | Kamoto |
| 2008/0268194 A1 | 10/2008 | Kim et al. |
| 2008/0274227 A1 | 11/2008 | Boatman et al. |
| 2008/0281287 A1 | 11/2008 | Marcelo |
| 2008/0294140 A1 | 11/2008 | Ecker et al. |
| 2008/0312617 A1 | 12/2008 | Hundorf et al. |
| 2008/0312618 A1 | 12/2008 | Hundorf et al. |
| 2008/0312619 A1 | 12/2008 | Hundorf et al. |
| 2008/0312620 A1 | 12/2008 | Ashton et al. |
| 2008/0312621 A1 | 12/2008 | Hundorf et al. |
| 2008/0312622 A1 | 12/2008 | Hundorf et al. |
| 2008/0312623 A1 | 12/2008 | Hundorf et al. |
| 2008/0312624 A1 | 12/2008 | Hundorf et al. |
| 2008/0312625 A1 | 12/2008 | Hundorf et al. |
| 2008/0312627 A1 | 12/2008 | Takeuchi |
| 2008/0312628 A1 | 12/2008 | Hundorf et al. |
| 2009/0023848 A1 | 1/2009 | Ahmed et al. |
| 2009/0056867 A1 | 3/2009 | Moriura et al. |
| 2009/0062760 A1 | 3/2009 | Wright et al. |
| 2009/0112173 A1 | 4/2009 | Bissah |
| 2009/0112175 A1 | 4/2009 | Bissah et al. |
| 2009/0157022 A1 | 6/2009 | Macdonald |
| 2009/0192035 A1 | 7/2009 | Stueven et al. |
| 2009/0240220 A1 | 9/2009 | Macdonald |
| 2009/0247977 A1 | 10/2009 | Takeuchi |
| 2009/0258994 A1 | 10/2009 | Stueven et al. |
| 2009/0270825 A1 | 10/2009 | Wciorka et al. |
| 2009/0298963 A1 | 12/2009 | Matsumoto et al. |
| 2009/0299312 A1 | 12/2009 | Macdonald |
| 2009/0306618 A1 | 12/2009 | Kudo |
| 2009/0318884 A1 | 12/2009 | Meyer et al. |
| 2010/0062165 A1 | 3/2010 | Suzuki |
| 2010/0062934 A1 | 3/2010 | Suzuki |
| 2010/0063470 A1 | 3/2010 | Suzuki |
| 2010/0068520 A1 | 3/2010 | Stueven et al. |
| 2010/0051166 A1 | 4/2010 | Hundorf et al. |
| 2010/0100065 A1 | 4/2010 | Bianco |
| 2010/0115237 A1 | 5/2010 | Brewer et al. |
| 2010/0121296 A1 | 5/2010 | Noda |
| 2010/0137773 A1 | 6/2010 | Gross |
| 2010/0137823 A1 | 6/2010 | Corneliusson |
| 2010/0198179 A1 | 8/2010 | Noda |
| 2010/0228210 A1 | 9/2010 | Busam et al. |
| 2010/0241096 A1 | 9/2010 | LaVon et al. |
| 2010/0241097 A1 | 9/2010 | Nigam et al. |
| 2010/0262099 A1 | 10/2010 | Klofta |
| 2010/0274208 A1 | 10/2010 | Gabrielii |
| 2010/0274210 A1 | 10/2010 | Noda |
| 2010/0312208 A1 | 12/2010 | Bond et al. |
| 2010/0324521 A1 | 12/2010 | Mukai |
| 2010/0324523 A1 | 12/2010 | Mukai |
| 2011/0041999 A1 | 2/2011 | Hundorf et al. |
| 2011/0060303 A1 | 3/2011 | Bissah |
| 2011/0066127 A1 | 3/2011 | Kuwano |
| 2011/0071486 A1 | 3/2011 | Harada |
| 2011/0092944 A1 | 4/2011 | Sagisaka |
| 2011/0112498 A1 | 5/2011 | Nhan et al. |
| 2011/0125120 A1 | 5/2011 | Nishitani |
| 2011/0130732 A1 | 6/2011 | Jackels et al. |
| 2011/0130737 A1 | 6/2011 | Sagisaka |
| 2011/0137276 A1 | 6/2011 | Yoshikawa |
| 2011/0144602 A1 | 6/2011 | Long |
| 2011/0144604 A1 | 6/2011 | Noda |
| 2011/0144606 A1 | 6/2011 | Nandrea |
| 2011/0152813 A1 | 6/2011 | Ellingson |
| 2011/0166540 A1 | 7/2011 | Yang et al. |
| 2011/0172630 A1 | 7/2011 | Nomoto |
| 2011/0174430 A1 | 7/2011 | Zhao |
| 2011/0208147 A1 | 8/2011 | Kawakami et al. |
| 2011/0250413 A1 | 10/2011 | Lu et al. |
| 2011/0268932 A1 | 11/2011 | Catalan et al. |
| 2011/0274834 A1 | 11/2011 | Brown et al. |
| 2011/0288513 A1 | 11/2011 | Hundorf et al. |
| 2011/0288514 A1 | 11/2011 | Kuroda |
| 2011/0295222 A1 | 12/2011 | Becker et al. |
| 2011/0319846 A1 | 12/2011 | Rinnert et al. |
| 2011/0319848 A1 | 12/2011 | McKiernan et al. |
| 2011/0319851 A1 | 12/2011 | Kudo |
| 2012/0004633 A1 | 1/2012 | Marcelo |
| 2012/0016326 A1 | 1/2012 | Brennan et al. |
| 2012/0022479 A1 | 1/2012 | Cotton |
| 2012/0035566 A1 | 2/2012 | Sagisaka |
| 2012/0035576 A1 | 2/2012 | Ichikawa |
| 2012/0064792 A1 | 3/2012 | Bauduin |
| 2012/0071848 A1 | 3/2012 | Zhang |
| 2012/0165771 A1 | 6/2012 | Ruman et al. |
| 2012/0165776 A1 | 6/2012 | McGregor et al. |
| 2012/0175056 A1 | 7/2012 | Tsang |
| 2012/0184934 A1 | 7/2012 | Venturino |
| 2012/0232514 A1 | 9/2012 | Baker |
| 2012/0238977 A1 | 9/2012 | Oku |
| 2012/0253306 A1 | 10/2012 | Otsubo |
| 2012/0256750 A1 | 10/2012 | Novak |
| 2012/0271262 A1 | 10/2012 | Venturino |
| 2012/0312491 A1 | 12/2012 | Jackels et al. |
| 2012/0316046 A1 | 12/2012 | Jackels et al. |
| 2012/0316523 A1 | 12/2012 | Hippe et al. |
| 2012/0316526 A1 | 12/2012 | Rosati et al. |
| 2012/0316527 A1 | 12/2012 | Rosati et al. |
| 2012/0316528 A1 | 12/2012 | Kreuzer et al. |
| 2012/0316529 A1 | 12/2012 | Kreuzer et al. |
| 2012/0323195 A1 | 12/2012 | Ehrnsperger et al. |
| 2012/0323201 A1 | 12/2012 | Bissah |
| 2012/0323202 A1 | 12/2012 | Bissah |
| 2013/0035656 A1 | 2/2013 | Moriya et al. |
| 2013/0041334 A1 | 2/2013 | Prioleau |
| 2013/0211354 A1 | 8/2013 | Tsuji et al. |
| 2013/0218115 A1 | 8/2013 | Katsuragawa et al. |
| 2013/0226119 A1 | 8/2013 | Katsuragawa et al. |
| 2013/0226120 A1 | 8/2013 | Van De Maele |
| 2014/0005622 A1 | 1/2014 | Wirtz et al. |
| 2014/0005623 A1 | 1/2014 | Wirtz et al. |
| 2014/0027066 A1 | 1/2014 | Jackels et al. |
| 2014/0039437 A1 | 2/2014 | Van De Maele |
| 2014/0045683 A1 | 2/2014 | Loick et al. |
| 2014/0135726 A1 | 5/2014 | Busam et al. |
| 2014/0142531 A1 | 5/2014 | Sasayama et al. |
| 2014/0163500 A1 | 6/2014 | Roe et al. |
| 2014/0163501 A1 | 6/2014 | Ehrnsperger et al. |
| 2014/0163502 A1 | 6/2014 | Arizti et al. |
| 2014/0163503 A1 | 6/2014 | Arizti et al. |
| 2014/0163506 A1 | 6/2014 | Roe et al. |
| 2014/0163511 A1 | 6/2014 | Roe et al. |
| 2014/0171893 A1 | 6/2014 | Lawson et al. |
| 2014/0318694 A1 | 10/2014 | Blessing et al. |
| 2014/0324007 A1 | 10/2014 | Hundorf et al. |
| 2014/0324008 A1 | 10/2014 | Hundorf et al. |
| 2015/0065986 A1 | 3/2015 | Blessing et al. |

FOREIGN PATENT DOCUMENTS

| | | |
|---|---|---|
| CA | 2308961 | 11/2000 |
| CA | 2487027 | 12/2003 |
| CA | 2561521 | 3/2007 |

(56) References Cited

FOREIGN PATENT DOCUMENTS

| | | |
|---|---|---|
| CA | 2630713 | 11/2008 |
| CA | 2636673 | 1/2009 |
| CA | 2712563 | 8/2010 |
| CA | 2702001 | 10/2010 |
| CN | 1238171 A | 12/1999 |
| CN | 2362468 Y | 2/2000 |
| CN | 1371671 | 2/2001 |
| CN | 2527254 Y | 12/2002 |
| CN | 2535020 Y | 2/2003 |
| CN | 2548609 Y | 5/2003 |
| CN | 1539391 | 10/2004 |
| CN | 1939242 | 4/2007 |
| CN | 101292930 | 10/2008 |
| CN | 201263750 | 7/2009 |
| CN | 201591689 | 9/2010 |
| CN | 201855366 U | 6/2011 |
| DE | 3205931 C2 | 9/1983 |
| DE | 3608114 A1 | 9/1987 |
| DE | 19732499 | 2/1999 |
| DE | 10204937 A1 | 8/2003 |
| EP | 083022 | 7/1983 |
| EP | 149880 | 7/1985 |
| EP | 0149880 A2 | 7/1985 |
| EP | 203289 | 12/1986 |
| EP | 0203289 A2 | 12/1986 |
| EP | 0206208 | 12/1986 |
| EP | 209561 B1 | 1/1987 |
| EP | 297411 B1 | 1/1989 |
| EP | 304957 | 3/1989 |
| EP | 374542 | 6/1990 |
| EP | 394274 | 10/1990 |
| EP | 0403832 | 12/1990 |
| EP | 481322 B1 | 4/1992 |
| EP | 530438 | 3/1993 |
| EP | 547847 | 6/1993 |
| EP | 555346 | 8/1993 |
| EP | 559476 | 9/1993 |
| EP | 591647 B2 | 4/1994 |
| EP | 597273 B1 | 5/1994 |
| EP | 601610 B2 | 6/1994 |
| EP | 632068 | 1/1995 |
| EP | 0640330 A1 | 3/1995 |
| EP | 0668066 | 9/1995 |
| EP | 685214 | 12/1995 |
| EP | 687453 | 12/1995 |
| EP | 0689817 | 1/1996 |
| EP | 0691133 | 1/1996 |
| EP | 0394274 | 7/1996 |
| EP | 724418 | 8/1996 |
| EP | 725613 | 8/1996 |
| EP | 725615 | 8/1996 |
| EP | 725616 | 8/1996 |
| EP | 758543 | 2/1997 |
| EP | 0761194 | 3/1997 |
| EP | 769284 | 4/1997 |
| EP | 0781537 | 7/1997 |
| EP | 783877 B1 | 7/1997 |
| EP | 787472 | 8/1997 |
| EP | 788874 B1 | 8/1997 |
| EP | 796068 | 9/1997 |
| EP | 799004 | 10/1997 |
| EP | 822794 B1 | 2/1998 |
| EP | 826351 | 3/1998 |
| EP | 844861 | 6/1998 |
| EP | 0737055 | 8/1998 |
| EP | 863733 | 9/1998 |
| EP | 971751 | 9/1998 |
| EP | 0875224 | 11/1998 |
| EP | 875224 A1 | 11/1998 |
| EP | 880955 | 12/1998 |
| EP | 891758 | 1/1999 |
| EP | 0893115 | 1/1999 |
| EP | 0724418 | 3/1999 |
| EP | 0725613 | 3/1999 |
| EP | 0725616 | 3/1999 |
| EP | 904755 | 3/1999 |
| EP | 0916327 | 5/1999 |
| EP | 925769 A2 | 6/1999 |
| EP | 933074 | 8/1999 |
| EP | 937736 | 8/1999 |
| EP | 941157 | 9/1999 |
| EP | 947549 | 10/1999 |
| EP | 951887 B1 | 10/1999 |
| EP | 0951890 | 10/1999 |
| EP | 2295493 | 10/1999 |
| EP | 2305749 | 10/1999 |
| EP | 2330152 | 10/1999 |
| EP | 953326 | 11/1999 |
| EP | 0978263 A1 | 2/2000 |
| EP | 985397 B1 | 3/2000 |
| EP | 0778762 | 4/2000 |
| EP | 1005847 | 6/2000 |
| EP | 1008333 | 6/2000 |
| EP | 1013252 B1 | 6/2000 |
| EP | 1018999 | 7/2000 |
| EP | 1019002 B1 | 7/2000 |
| EP | 1019003 B1 | 7/2000 |
| EP | 1022008 | 7/2000 |
| EP | 1023884 | 8/2000 |
| EP | 1053729 | 11/2000 |
| EP | 1059072 A2 | 12/2000 |
| EP | 1063954 | 1/2001 |
| EP | 1071388 | 1/2001 |
| EP | 1078618 | 2/2001 |
| EP | 1088537 A2 | 4/2001 |
| EP | 0796068 | 5/2001 |
| EP | 752892 | 7/2001 |
| EP | 1116479 A2 | 7/2001 |
| EP | 0790839 | 8/2001 |
| EP | 1132069 | 9/2001 |
| EP | 1173128 | 1/2002 |
| EP | 1175194 B1 | 1/2002 |
| EP | 1184018 | 3/2002 |
| EP | 1192312 B1 | 4/2002 |
| EP | 1196122 B2 | 4/2002 |
| EP | 1199059 | 4/2002 |
| EP | 1199327 | 4/2002 |
| EP | 1208824 | 5/2002 |
| EP | 0793469 | 6/2002 |
| EP | 1210925 | 6/2002 |
| EP | 1224922 | 7/2002 |
| EP | 1225857 | 7/2002 |
| EP | 1253231 | 10/2002 |
| EP | 1262531 A1 | 12/2002 |
| EP | 1263374 B1 | 12/2002 |
| EP | 0737056 | 1/2003 |
| EP | 1275358 | 1/2003 |
| EP | 1275361 | 1/2003 |
| EP | 1293187 | 3/2003 |
| EP | 1304986 B1 | 5/2003 |
| EP | 1332742 B1 | 8/2003 |
| EP | 1339368 | 9/2003 |
| EP | 1374817 | 1/2004 |
| EP | 1388334 | 2/2004 |
| EP | 1402863 | 3/2004 |
| EP | 962208 | 8/2004 |
| EP | 1447066 | 8/2004 |
| EP | 1447067 | 8/2004 |
| EP | 1460987 | 9/2004 |
| EP | 963749 | 11/2004 |
| EP | 1495739 | 1/2005 |
| EP | 1524955 | 4/2005 |
| EP | 1920743 | 4/2005 |
| EP | 1541103 | 6/2005 |
| EP | 1551344 | 7/2005 |
| EP | 1586289 | 10/2005 |
| EP | 1588723 | 10/2005 |
| EP | 1605882 | 12/2005 |
| EP | 1609448 | 12/2005 |
| EP | 1621166 | 2/2006 |
| EP | 1621167 | 2/2006 |
| EP | 1632206 | 3/2006 |
| EP | 1642556 | 4/2006 |
| EP | 1403419 | 5/2006 |

(56) References Cited

FOREIGN PATENT DOCUMENTS

| | | |
|---|---|---|
| EP | 1656162 | 5/2006 |
| EP | 1669046 | 6/2006 |
| EP | 1688114 | 8/2006 |
| EP | 2314265 | 8/2006 |
| EP | 1723939 | 11/2006 |
| EP | 1738727 | 1/2007 |
| EP | 1754461 | 2/2007 |
| EP | 1787611 | 5/2007 |
| EP | 1813238 | 8/2007 |
| EP | 2008626 | 12/2008 |
| EP | 2055279 A1 | 5/2009 |
| EP | 2093049 | 8/2009 |
| EP | 2130522 | 12/2009 |
| EP | 1621165 | 4/2010 |
| EP | 2444046 | 4/2012 |
| EP | 2532328 | 12/2012 |
| EP | 2532329 A1 | 12/2012 |
| EP | 2532332 A1 | 12/2012 |
| EP | 2679210 A1 | 1/2014 |
| EP | 2740449 | 6/2014 |
| EP | 2740450 | 6/2014 |
| EP | 2740452 | 6/2014 |
| ES | 2213491 | 8/2004 |
| FR | 2566631 | 1/1986 |
| FR | 2583377 | 12/1986 |
| FR | 2612770 | 9/1988 |
| FR | 2810234 | 12/2001 |
| GB | 1333081 A | 8/1971 |
| GB | 1307441 | 2/1973 |
| GB | 1513055 | 6/1978 |
| GB | 2101468 | 1/1983 |
| GB | 2170108 | 7/1986 |
| GB | 2262873 | 7/1993 |
| GB | 2288540 A | 6/1994 |
| GB | 2354449 | 3/2001 |
| GB | 2452260 A | 10/2007 |
| GR | 851769 | 11/1985 |
| IN | 0984/KOL/1999 | 10/2005 |
| IN | 212479 B | 3/2007 |
| IN | 208543 B | 8/2007 |
| IN | 0980/MUM/2009 | 6/2009 |
| JP | 5572928 U | 5/1980 |
| JP | 598322 U | 1/1984 |
| JP | 630148323 U | 9/1988 |
| JP | 2107250 | 4/1990 |
| JP | 03224481 B2 | 10/1991 |
| JP | 04122256 | 4/1992 |
| JP | 04341368 | 11/1992 |
| JP | 06191505 | 7/1994 |
| JP | 06269475 A | 9/1994 |
| JP | 07124193 | 5/1995 |
| JP | 08215629 | 8/1996 |
| JP | 10328232 | 12/1998 |
| JP | 11-033056 A | 2/1999 |
| JP | 11318980 | 11/1999 |
| JP | 11320742 | 11/1999 |
| JP | 2000232985 | 8/2000 |
| JP | 2000238161 | 9/2000 |
| JP | 2001-046435 A | 2/2001 |
| JP | 2001037810 | 2/2001 |
| JP | 2001120597 | 5/2001 |
| JP | 2001158074 | 6/2001 |
| JP | 2001178768 A | 7/2001 |
| JP | 2001198157 | 7/2001 |
| JP | 2001224626 A | 8/2001 |
| JP | 2001277394 | 10/2001 |
| JP | 03420481 B2 | 11/2001 |
| JP | 2001321397 | 11/2001 |
| JP | 2001353174 A | 12/2001 |
| JP | 2002052042 A | 2/2002 |
| JP | 2002065718 | 3/2002 |
| JP | 2002113800 A | 4/2002 |
| JP | 2002165832 | 6/2002 |
| JP | 2002165836 | 6/2002 |
| JP | 2002178429 | 6/2002 |
| JP | 2002272769 A | 9/2002 |
| JP | 2002320641 | 11/2002 |
| JP | 2002325792 A | 11/2002 |
| JP | 2002325799 A | 11/2002 |
| JP | 2002-369841 A | 12/2002 |
| JP | 2003126140 | 5/2003 |
| JP | 2003153955 A | 5/2003 |
| JP | 2003265523 | 9/2003 |
| JP | 2003265524 A | 9/2003 |
| JP | 2003275237 | 9/2003 |
| JP | 2004089269 | 3/2004 |
| JP | 03566012 B2 | 6/2004 |
| JP | 03568146 B2 | 6/2004 |
| JP | 03616077 B2 | 11/2004 |
| JP | 2004-337385 A | 12/2004 |
| JP | 2004337314 A | 12/2004 |
| JP | 2004350864 | 12/2004 |
| JP | 03640475 B2 | 1/2005 |
| JP | 2005000312 A | 1/2005 |
| JP | 03660816 B2 | 3/2005 |
| JP | 03676219 B2 | 5/2005 |
| JP | 03688403 B2 | 6/2005 |
| JP | 03705943 B2 | 8/2005 |
| JP | 03719819 B2 | 9/2005 |
| JP | 03724963 B2 | 9/2005 |
| JP | 03725008 B2 | 9/2005 |
| JP | 03737376 B2 | 11/2005 |
| JP | 2006014792 A | 1/2006 |
| JP | 03781617 B2 | 3/2006 |
| JP | 2006110329 | 4/2006 |
| JP | 2006513824 T | 4/2006 |
| JP | 03801449 B2 | 5/2006 |
| JP | 2006116036 A | 5/2006 |
| JP | 03850102 B2 | 9/2006 |
| JP | 03850207 B2 | 9/2006 |
| JP | 03856941 B2 | 9/2006 |
| JP | 03868628 B2 | 10/2006 |
| JP | 03874499 B2 | 11/2006 |
| JP | 03877702 B2 | 11/2006 |
| JP | 2006325639 A | 12/2006 |
| JP | 2006346021 | 12/2006 |
| JP | 03904356 B2 | 1/2007 |
| JP | 2007007455 A | 1/2007 |
| JP | 2007007456 A | 1/2007 |
| JP | 03926042 B2 | 3/2007 |
| JP | 03934855 B2 | 3/2007 |
| JP | 2007089906 A | 4/2007 |
| JP | 2007105198 A | 4/2007 |
| JP | 2007152033 A | 6/2007 |
| JP | 03986210 B2 | 7/2007 |
| JP | 03986222 B2 | 7/2007 |
| JP | 2007167453 | 7/2007 |
| JP | 2007175515 A | 7/2007 |
| JP | 2007195665 A | 8/2007 |
| JP | 2007267763 A | 10/2007 |
| JP | 2007275491 A | 10/2007 |
| JP | 04035341 B2 | 11/2007 |
| JP | 04058281 B2 | 12/2007 |
| JP | 04061086 B2 | 12/2007 |
| JP | 04092319 B2 | 3/2008 |
| JP | 2008080150 A | 4/2008 |
| JP | 2008093289 A | 4/2008 |
| JP | 04124322 B2 | 5/2008 |
| JP | 2008119081 A | 5/2008 |
| JP | 2008136739 A | 6/2008 |
| JP | 2008136877 A | 6/2008 |
| JP | 04148594 B2 | 7/2008 |
| JP | 04148620 B2 | 7/2008 |
| JP | 2008154606 A | 7/2008 |
| JP | 04162609 B2 | 8/2008 |
| JP | 04162637 B2 | 8/2008 |
| JP | 04166923 B2 | 8/2008 |
| JP | 04167406 B2 | 8/2008 |
| JP | 04173723 B2 | 8/2008 |
| JP | 04190675 B2 | 9/2008 |
| JP | 04190693 B2 | 9/2008 |
| JP | 04208338 B2 | 10/2008 |
| JP | 2008246089 | 10/2008 |
| JP | 04230971 B2 | 12/2008 |

(56) References Cited

FOREIGN PATENT DOCUMENTS

| | | |
|---|---|---|
| JP | 2008295475 A | 12/2008 |
| JP | 2008295713 A | 12/2008 |
| JP | 04261593 B2 | 2/2009 |
| JP | 2009112590 | 5/2009 |
| JP | 04322228 B2 | 6/2009 |
| JP | 2009136601 | 6/2009 |
| JP | 2009142401 A | 7/2009 |
| JP | 2009201878 A | 9/2009 |
| JP | 2009-232987 A | 10/2009 |
| JP | 04392936 B2 | 10/2009 |
| JP | 2009261777 A | 11/2009 |
| JP | 2009291473 A | 12/2009 |
| JP | 2009297048 A | 12/2009 |
| JP | 2010017342 | 1/2010 |
| JP | 04458702 B2 | 2/2010 |
| JP | 04459013 B2 | 2/2010 |
| JP | 2010022560 | 2/2010 |
| JP | 04481325 B2 | 3/2010 |
| JP | 2010051654 A | 3/2010 |
| JP | 2010063814 A | 3/2010 |
| JP | 2010063944 A | 3/2010 |
| JP | 2010-075462 A | 4/2010 |
| JP | 04492957 B2 | 4/2010 |
| JP | 2010068954 A | 4/2010 |
| JP | 2010082059 A | 4/2010 |
| JP | 2010104545 A | 5/2010 |
| JP | 2010104547 A | 5/2010 |
| JP | 2010110535 A | 5/2010 |
| JP | 2010119454 A | 6/2010 |
| JP | 2010119605 A | 6/2010 |
| JP | 2010119743 A | 6/2010 |
| JP | 2010131131 A | 6/2010 |
| JP | 2010131132 A | 6/2010 |
| JP | 2010131206 | 6/2010 |
| JP | 2010131297 A | 6/2010 |
| JP | 2010136917 A | 6/2010 |
| JP | 2010136973 A | 6/2010 |
| JP | 04540563 B2 | 7/2010 |
| JP | 2010-194124 A | 9/2010 |
| JP | 04587947 B2 | 9/2010 |
| JP | 2010201093 | 9/2010 |
| JP | 2010221067 | 10/2010 |
| JP | 04620299 B2 | 11/2010 |
| JP | 04627472 B2 | 11/2010 |
| JP | 04627473 B2 | 11/2010 |
| JP | 04638087 B2 | 12/2010 |
| JP | 04652626 B2 | 12/2010 |
| JP | 2010273842 A | 12/2010 |
| JP | 2010284418 A | 12/2010 |
| JP | 2011000480 A | 1/2011 |
| JP | 2011030700 | 2/2011 |
| JP | 04693574 B2 | 3/2011 |
| JP | 2011067484 A | 4/2011 |
| JP | 2011072720 A | 4/2011 |
| JP | 2011104014 | 6/2011 |
| JP | 2011104122 A | 6/2011 |
| JP | 2011120661 A | 6/2011 |
| JP | 2011125360 A | 6/2011 |
| JP | 2011125537 | 6/2011 |
| JP | 04776516 B2 | 7/2011 |
| JP | 2011130797 A | 7/2011 |
| JP | 2011130799 A | 7/2011 |
| JP | 2011156032 A | 8/2011 |
| JP | 2011156070 A | 8/2011 |
| JP | 2011156254 | 8/2011 |
| JP | 04824882 B2 | 9/2011 |
| JP | 4850272 B2 | 10/2011 |
| JP | 04855533 B2 | 11/2011 |
| JP | 2011239858 | 12/2011 |
| JP | 04931572 B2 | 2/2012 |
| JP | 04937225 B2 | 3/2012 |
| JP | 04953618 B2 | 3/2012 |
| JP | 04969437 B2 | 4/2012 |
| JP | 04969640 B2 | 4/2012 |
| JP | 4971491 B2 | 4/2012 |
| JP | 04974524 B2 | 4/2012 |
| JP | 04979780 B2 | 4/2012 |
| JP | 05016020 B2 | 6/2012 |
| JP | 05027364 B2 | 6/2012 |
| JP | 05031082 B2 | 7/2012 |
| JP | 05042351 B2 | 7/2012 |
| JP | 05043569 B2 | 7/2012 |
| JP | 05043591 B2 | 7/2012 |
| JP | 05046488 B2 | 7/2012 |
| JP | 2012125625 A | 7/2012 |
| JP | 05053765 B2 | 8/2012 |
| JP | 05070275 B2 | 8/2012 |
| JP | 05079931 B1 | 9/2012 |
| JP | 05080189 B2 | 9/2012 |
| JP | 05084442 B2 | 9/2012 |
| JP | 05084476 B2 | 9/2012 |
| JP | 5085770 B2 | 9/2012 |
| JP | 05089269 B2 | 9/2012 |
| JP | 05113146 B2 | 10/2012 |
| JP | 05129536 B2 | 11/2012 |
| JP | 05105884 B2 | 12/2012 |
| KR | 20010005620 | 1/2001 |
| KR | 20020035634 | 5/2002 |
| KR | 20080028771 | 4/2008 |
| SE | 9400916 | 3/1994 |
| SE | 9704893 | 12/1997 |
| WO | WO9015830 | 12/1990 |
| WO | WO9219198 | 11/1992 |
| WO | WO9321237 | 10/1993 |
| WO | WO9321879 | 11/1993 |
| WO | WO9510996 | 4/1995 |
| WO | WO9511652 | 5/1995 |
| WO | WO9514453 | 6/1995 |
| WO | WO9515139 | 6/1995 |
| WO | WO9516424 | 6/1995 |
| WO | WO9516746 | 6/1995 |
| WO | WO9519753 | 7/1995 |
| WO | WO9521596 | 8/1995 |
| WO | WO9524173 | 9/1995 |
| WO | WO9526209 | 10/1995 |
| WO | WO9529657 | 11/1995 |
| WO | WO9532698 | 12/1995 |
| WO | WO9534329 | 12/1995 |
| WO | WO9616624 | 6/1996 |
| WO | WO9619173 | 6/1996 |
| WO | WO9629967 | 10/1996 |
| WO | WO9711659 | 4/1997 |
| WO | WO9717922 | 5/1997 |
| WO | WO9816179 | 4/1998 |
| WO | WO9816180 | 4/1998 |
| WO | WO9843684 | 10/1998 |
| WO | WO9913813 | 3/1999 |
| WO | WO9934841 | 7/1999 |
| WO | WO9951178 | 10/1999 |
| WO | WO0000235 | 1/2000 |
| WO | WO0032145 | 6/2000 |
| WO | WO0059430 | 10/2000 |
| WO | WO0115647 | 3/2001 |
| WO | WO0126596 | 4/2001 |
| WO | WO0207663 | 1/2002 |
| WO | WO0232962 | 4/2002 |
| WO | WO02064877 | 8/2002 |
| WO | WO02067809 | 9/2002 |
| WO | WO03009794 | 2/2003 |
| WO | WO03039402 | 5/2003 |
| WO | WO03053297 | 7/2003 |
| WO | WO03079946 | 10/2003 |
| WO | WO03101622 | 12/2003 |
| WO | WO03105738 | 12/2003 |
| WO | WO2004021946 | 3/2004 |
| WO | WO2004049995 | 6/2004 |
| WO | WO2004071539 | 8/2004 |
| WO | WO2004084784 | 10/2004 |
| WO | WO2004105664 | 12/2004 |
| WO | WO2005/018694 | 3/2005 |
| WO | WO2005087164 | 9/2005 |
| WO | WO2006104024 | 5/2006 |
| WO | WO2006059922 | 6/2006 |
| WO | WO2006062258 | 6/2006 |

(56) References Cited

FOREIGN PATENT DOCUMENTS

| | | |
|---|---|---|
| WO | WO2006066029 | 6/2006 |
| WO | WO2006083584 | 8/2006 |
| WO | WO2006134904 | 12/2006 |
| WO | WO2006134906 | 12/2006 |
| WO | WO2007000315 | 1/2007 |
| WO | WO2007046052 | 4/2007 |
| WO | WO2007047598 | 4/2007 |
| WO | WO2007049725 | 5/2007 |
| WO | WO2007061035 | 5/2007 |
| WO | WO2007142145 | 12/2007 |
| WO | WO2007148502 | 12/2007 |
| WO | WO2008018922 | 2/2008 |
| WO | WO2008065945 | 6/2008 |
| WO | WO2008146749 | 12/2008 |
| WO | WO2008155699 | 12/2008 |
| WO | WO2009004941 | 1/2009 |
| WO | WO2009005431 | 1/2009 |
| WO | WO2009139248 | 1/2009 |
| WO | WO2009139255 | 1/2009 |
| WO | WO2009041223 | 4/2009 |
| WO | WO2009096108 | 8/2009 |
| WO | WO2009107435 | 9/2009 |
| WO | WO2009122830 | 10/2009 |
| WO | WO2009152018 | 12/2009 |
| WO | WO2009155264 | 12/2009 |
| WO | WO2009155265 | 12/2009 |
| WO | WO2010071508 | 6/2010 |
| WO | WO2010074319 | 7/2010 |
| WO | WO2010107096 | 9/2010 |
| WO | WO2010114052 | 10/2010 |
| WO | WO2010117015 | 10/2010 |
| WO | WO201153044 | 5/2011 |
| WO | WO2011118725 | 9/2011 |
| WO | WO2011118842 | 9/2011 |
| WO | WO2011145653 | 11/2011 |
| WO | WO 2011/150955 | 12/2011 |
| WO | WO2011163582 | 12/2011 |
| WO | WO2012002252 | 1/2012 |
| WO | WO2012014436 | 2/2012 |
| WO | WO2012042908 | 4/2012 |
| WO | WO2012043077 | 4/2012 |
| WO | WO2012043078 | 4/2012 |
| WO | WO2012052172 | 4/2012 |
| WO | WO2012043082 | 5/2012 |
| WO | WO2012067216 | 5/2012 |
| WO | WO2012073499 | 6/2012 |
| WO | WO2012074466 | 6/2012 |
| WO | WO201291016 | 7/2012 |
| WO | WO2012090508 | 7/2012 |
| WO | WO2012101934 | 8/2012 |
| WO | WO2012102034 | 8/2012 |
| WO | WO2012117824 | 9/2012 |
| WO | WO2012132460 | 10/2012 |
| WO | WO2012170778 | 12/2012 |
| WO | WO2012170779 | 12/2012 |
| WO | WO2012170781 | 12/2012 |
| WO | WO2012170808 | 12/2012 |
| WO | WO2012174026 | 12/2012 |
| WO | WO2013001788 | 1/2013 |
| WO | WO2013060733 | 5/2013 |
| WO | WO2014078247 | 5/2014 |

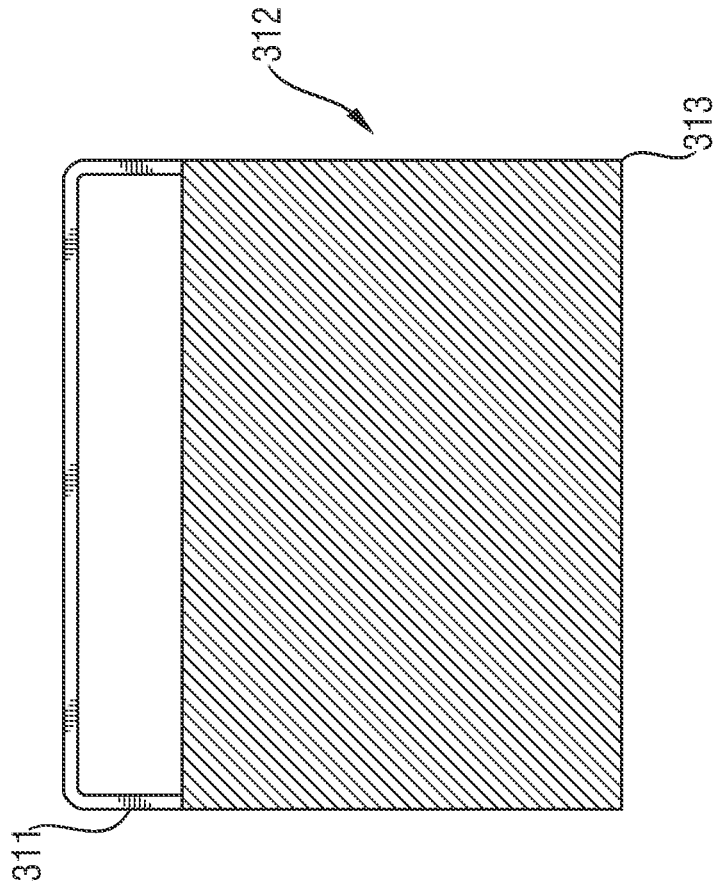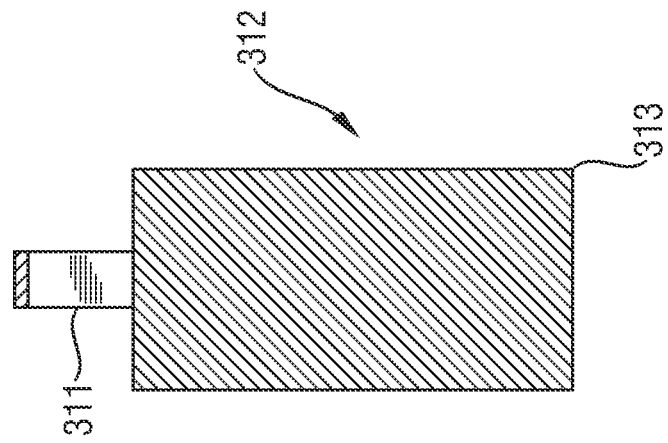

DISPOSABLE DIAPER HAVING REDUCED ABSORBENT CORE TO BACKSHEET GLUING

FIELD

The present disclosure generally relates to disposable diaper having absorbent cores comprising superabsorbent polymer particles which are immobilized by adhesive. The absorbent core is attached to the backsheet of the disposable diaper only in certain attachment zones to reduce see-through and the formation of tension lines on the backsheet.

BACKGROUND

The use of superabsorbent polymer material in disposable diapers is generally known. The use of superabsorbent polymer material facilitates disposable diapers having a thinner absorbent core versus the use of absorbent materials such as fluff pulp, especially while the disposable diaper is in the dry state.

Today, most disposable diapers which are commercially available still have absorbent cores containing a mixture of so-called airfelt (cellulose fibers) and superabsorbent polymer particles. The cellulose fibers comprised by the absorbent core generally hold the superabsorbent polymer particles in place as the cellulose fibers entangle the particles such that the particles are trapped between the cellulose fibers. This generally does not result in a complete immobilization of the superabsorbent polymer particles, as the particles still may have some degree of freedom to move within the interstices between the cellulose fibers. However, the superabsorbent polymer particles are held in the desired position to a sufficiently satisfying degree.

Using higher amounts of superabsorbent polymer particles is desirable as it enables thinner absorbent cores. However, in absorbent cores having high amounts of superabsorbent polymer particles and little or no airfelt, the superabsorbent polymer particles can no longer be held in place in the interstices between the cellulose fibers, as the ratio of superabsorbent polymer particles to cellulose fibers is too high. Therefore, in absorbent cores having very high amounts of superabsorbent polymer particles (such as >80%), the particles have to be immobilized by some other means. One way to facilitate immobilization is the use of adhesive, such as hot melt adhesive. The hot melt adhesive may be applied as a fine, fibrous network within the absorbent core. Further, in absorbent cores having a high percentage of superabsorbent polymer material and little or no airfelt the superabsorbent polymer material is often sandwiched between carrier substrates. The carrier substrates are typically nonwoven webs.

Absorbent cores having relatively high amounts of superabsorbent polymer particles immobilized by hot melt adhesive and having little or no airfelt have few to no interstices (e.g. those provided between cellulose fibers). Thus, there is no available "free space" within the absorbent core into which the superabsorbent polymer particles can expand upon absorption of liquid. In these absorbent cores the superabsorbent polymer particles, upon swelling, will exert a certain force onto the nonwoven webs, which typically enwrap and encompass the superabsorbent polymer particles. Consequently, the nonwoven webs will also elongate in order to accommodate for the additional space needed by the swelling superabsorbent polymer particles within the absorbent core.

It has been found that an elongated and somewhat strained absorbent core, when incorporated in a disposable diaper, which has been attached onto a wearer, may result in a strained appearance of the backsheet, leading e.g. to the formation of tension lines or wrinkles. Such tensed appearance may give raise to concerns by wearers or—if the wearers are babies or toddles—by the caretakers regarding the overall quality and especially the capacity of the disposable diaper. The tensed appearance may be perceived as an indication that the disposable diaper has reached its maximum load and needs to be replaced even if in fact a considerable amount of absorbent capacity is still available. The caretakers or wearers may thus attempt to change the diaper even if the absorbent core may still have the capacity to absorb further gushes of urine.

There is thus a need for disposable diapers with absorbent cores having high amounts of superabsorbent polymer particles and little to no airfelt, wherein, when only partly loaded with liquid, the backsheet may not have a strained appearance, especially when attached onto a wearer.

SUMMARY

The present disclosure generally relates to a disposable diaper comprising a backsheet, a topsheet and therein between an absorbent core. The absorbent core has a longitudinal direction with a longitudinal axis and perpendicular thereto a lateral direction with a transverse axis, and the absorbent core further has a front region, a back region and a crotch region therein between and a front lateral edge, an opposing back lateral edge, and longitudinally extending side edges.

The absorbent core comprises superabsorbent polymer particles, which are immobilized by a first core adhesive. The absorbent core is attached to the backsheet according to one of the following options:

The absorbent core is attached to backsheet of the disposable diaper in attachment zones adjacent to the front lateral edge and the back lateral edge of the absorbent core and the absorbent core is unattached to the backsheet in any other region; or The absorbent core is attached to the backsheet of the disposable diaper in the crotch region of the absorbent core in one or more than one attachment zone(s) on or adjacent to the longitudinal axis of the absorbent core, wherein the one or more than one attachment zone(s) cover from 0.2% to 3% of the total surface area of the absorbent core, and the absorbent core is unattached to the backsheet in any other region; or The absorbent core is attached to the backsheet of the disposable diaper in the crotch region of the absorbent core in attachment zones adjacent to the longitudinal side edges of the absorbent core and the absorbent core is unattached to the backsheet in any other region; or The absorbent core is attached to the backsheet of the disposable diaper in combinations of any of the attachment zones of a) to c) and the absorbent core is unattached to the backsheet in any other region.

BRIEF DESCRIPTION OF THE DRAWINGS

FIG. 8 is a schematic drawing of a weight used in the test method to visualize backsheet see-through (front view) in accordance with an embodiment of the present disclosure.

FIG. 9 is a schematic drawing of a weight used in the test method to visualize backsheet see-through (side view) in accordance with an embodiment of the present disclosure.

DETAILED DESCRIPTION

Definitions

Figure 1:
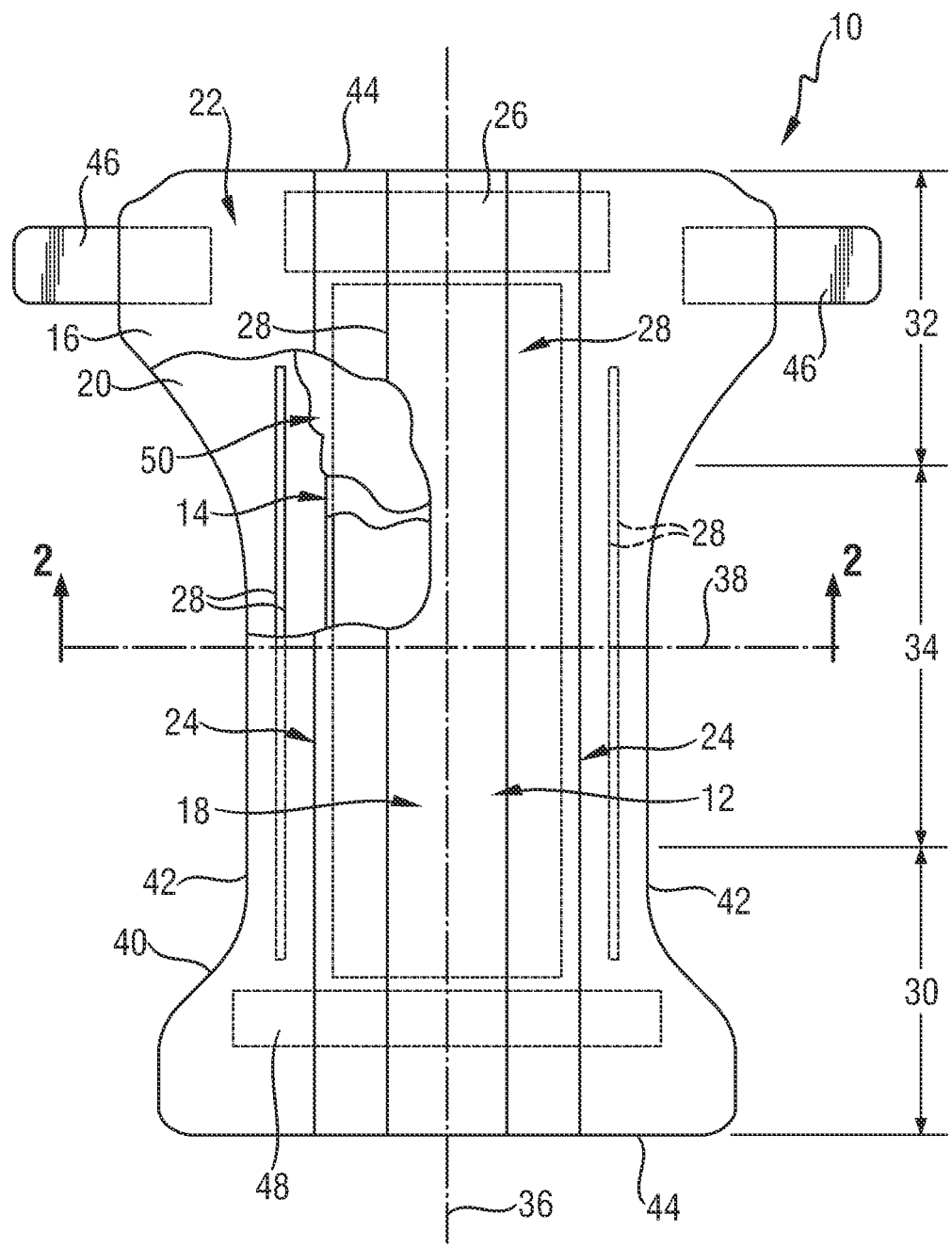
FIG. 1 is a plan view of a schematic drawing of a disposable diaper in accordance with an embodiment of the present disclosure.

"Absorbent core" means a structure that is disposed between a topsheet and a backsheet of a disposable diaper for absorbing and containing liquid received by the disposable diaper.

"Airfelt" is used herein to refer to comminuted wood pulp, which is a form of cellulose fibers (absorbent fibers).

"Diaper" refers to an absorbent article generally worn by infants and incontinent persons about the lower torso so as to encircle the waist and legs of the wearer and which is specifically adapted to receive and contain urinary and fecal waste. For the present disclosure, the term "diaper" is considered to encompass "diaper pants".

"Diaper-pant", as used herein, refers to disposable garments having a waist opening and leg openings designed for infant or adult wearers. A diaper-pant may be placed in position on the wearer by inserting the wearer's legs into the leg openings and sliding the pant into position about a wearer's lower torso. A diaper-pant may be preformed by any suitable technique including, but not limited to, joining together portions of the article using refastenable and/or non-refastenable bonds (e.g., seam, weld, adhesive, cohesive bond, fastener, etc.). A diaper-pant may be preformed anywhere along the circumference of the article (e.g., side fastened, front waist fastened). The terms "diaper-pant" is also commonly referred to as "prefastened diaper," "pull-on diaper," "training pant," and "pant".

"Disposable" is used in its ordinary sense to mean an article that is disposed or discarded after a limited number of usage events over varying lengths of time, for example, less than 10 events, less than 5 events, or less than 2 events. A disposable absorbent article is most often disposed after single use.

"Hot melt adhesive" as used herein refers to adhesives in alignment with the description given in "Adhesion and Adhesives Technology: An Introduction" by Alphonsus V. Pocius (Hanser publishers Munich, 1997). Therein a hot melt is defined as an adhesive applied from the melt and gaining strength upon solidification.

"Non-elastic" as used herein refers to a backsheet which does not recover by more than 20% if subjected to the following test:

A rectangular piece of backsheet material (such as a film or a nonwoven or—if the backsheet comprises a film and a nonwoven web—both materials taken together in the configuration in which they are used as backsheet material) having a width of 2.54 cm and a length of 25.4 cm is maintained in a vertical position by holding the piece along its upper 2.54 cm wide edge along its complete width. A force of 10 N is applied onto the opposite lower edge along the complete width of the material for 1 minute at 25° C.

Immediately after one minute, the length of the piece is measured while the force is still applied and the degree of elongation is calculated by subtracting the initial length (10 inch) from the length measured after one minute.

Immediately after the length of the rectangular piece has been measured, the force is removed and the piece is laid down flat on a table for 5 minutes (at 25° C.) to be able to recover. Immediately after 5 minutes, the length of the piece is measured again and the degree of elongation is calculated by subtracting the initial length (25.4 cm) from the length after 5 minutes.

The elongation after one minute while the force has been is compared to the elongation after the piece has been laid down flat on a table for 5 minutes: If the elongation does not recover by more than 20%, the material or element is considered to be "non-elastic".

"Highly non-elastic" as used herein refers to a material or element, which is either "non-extensible" or which does not recover by more than 10% if subjected to the test set out above for "non-elastic".

A "nonwoven web" is a manufactured sheet or web of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms such as short fibers (known as staple, or chopped), continuous single fibers (filaments or monofilaments), untwisted bundles of continuous filaments, and twisted bundles of continuous filaments (yarn). Nonwoven webs can be formed by many processes such as meltblowing, spunbonding, solvent spinning, electrospinning, carding and airlaying. Nonwoven webs may be bonded by heat and/or pressure or may be adhesively bonded. Bonding may be limited to certain areas of the nonwoven web (point bonding). Nonwoven webs may also be hydro-entangled or needle-punched. The basis weight of nonwoven webs is usually expressed in grams per square meter (gsm).

"Superabsorbent polymer particles" as used herein refers to substantially water-insoluble polymer particles that can absorb at least 5 times their weight of an aqueous 0.9% saline solution as measured using the Centrifuge Retention Capacity test (Edana 441.2-01). "Superabsorbent polymer particles" refer to an absorbent polymer material which is in particulate form so as to be flowable in the dry state.

Disposable Diaper

FIG. 1 is a plan view of a disposable diaper 10 according to a certain embodiment of the present disclosure. The disposable diaper 10 is shown in its flat out, uncontracted state (i.e. without elastic induced contraction) and portions of the disposable diaper 10 are cut away to more clearly show the underlying structure of the disposable diaper 10. A portion of the disposable diaper 10 that contacts a wearer is facing the viewer in FIG. 1. The disposable diaper 10 generally may comprise a chassis 12 and an absorbent core 14 disposed in the chassis 12.

The chassis 12 of the disposable diaper 10 in FIG. 1 comprises the main body of the disposable diaper 10. The chassis 12 may comprise an outer covering 16 including a topsheet 18, which may be liquid pervious, and/or a backsheet 20, which may be liquid impervious. The absorbent core 14 may be encased between the topsheet 18 and the backsheet 20. The chassis 12 may also include side panels 22, elasticized leg cuffs 24, and an elastic waist feature 26.

The leg cuffs 24 and the elastic waist feature 26 may each typically comprise elastic members 28 such as elastic strands. One end portion of the disposable diaper 10 is configured as a front waist region 30 of the disposable diaper 10. An opposite end portion of the disposable diaper 10 is configured as a back waist region 32 of the disposable diaper 10. An intermediate portion of the disposable diaper 10 is configured as a crotch region 34, which extends longitudinally between the first and second waist regions 30 and 32. The waist regions 30 and 32 may include elastic elements such that they gather about the waist of the wearer to provide improved fit and containment (elastic waist feature 26). The crotch region 34 is that portion of the disposable diaper 10 which, when the disposable diaper 10 is worn, is generally positioned between the wearer's legs.

The disposable diaper 10 is depicted in FIG. 1 with its longitudinal axis 36 and its transverse axis 38. The periphery 40 of the disposable diaper 10 is defined by the outer edges of the disposable diaper 10 in which the longitudinal edges 42 run generally parallel to the longitudinal axis 36 of the disposable diaper 10 and the end edges 44 run between the longitudinal edges 42 generally parallel to the transverse axis 38 of the disposable diaper 10. The disposable diaper 20 may also include such other features as are known in the art including front and back ear panels, waist cap features, elastics and the like to provide better fit, containment and aesthetic characteristics.

In order to keep the disposable diaper 10 in place about the wearer, at least a portion of the first waist region 30 may be attached by the fastening member 46 to at least a portion of the second waist region 32 to form leg opening(s) and an article waist. To this end, according to certain embodiments, the disposable diaper 10 may be provided with a re-closable fastening system or may alternatively be provided in the form of a disposable diaper-pant. When the absorbent article is a disposable diaper, it may comprise a re-closable fastening system joined to the chassis for securing the disposable diaper to a wearer. The fastening system may include at least one fastening member 46 and at least one landing zone 48. When the absorbent article is a disposable diaper-pant, the article may comprise two side panels on each waist region 30, 32 joined to the chassis along the longitudinal edges of the side panels which face towards the longitudinal axis 36. The side panels of the front waist region 30 are further joined to the respective side panels of the back waist region 32 along their longitudinal edges facing away from the longitudinal axis 36 to form a pant.

Figure 2:
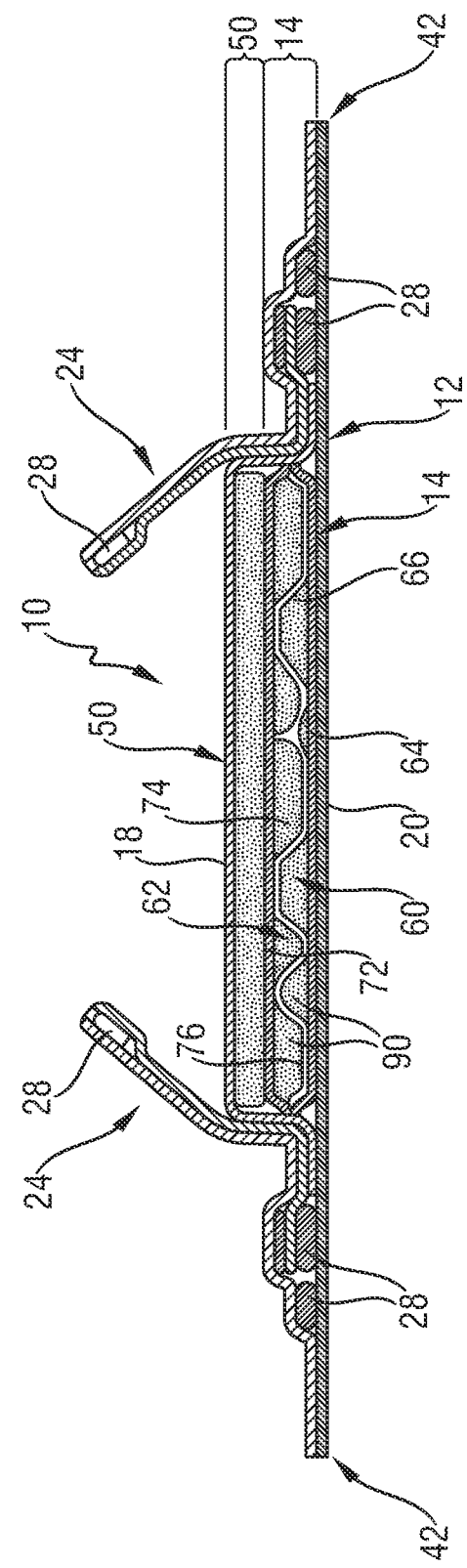
FIG. 2 is a cross sectional view of the disposable diaper shown in FIG. 1 taken along the sectional line 2-2 of FIG. 1 in accordance with an embodiment of the present disclosure.

A cross section of FIG. 1 along the sectional line 2-2 of FIG. 1 is shown in FIG. 2: Starting from the wearer facing side, the disposable diaper 10 may comprise the topsheet 18, the components of the absorbent core 14, and the backsheet 20. Disposable diaper 10 may also comprise an acquisition system 50 disposed between the liquid permeable topsheet 18 and the wearer facing side of the absorbent core 14. The acquisition system 50 may be in direct contact with the absorbent core.

The acquisition system 50 may comprise a single layer or multiple layers (not shown), such as an upper acquisition layer facing towards the wearer and a lower acquisition layer facing the garment of the wearer. According to a certain embodiment, the acquisition system 50 may function to receive a surge of liquid, such as a gush of urine. In other words, the acquisition system 50 may serve as a temporary reservoir for liquid until the absorbent core 14 can absorb the liquid.

In a certain embodiment, the acquisition system 50 may comprise chemically cross-linked cellulose fibers and/or nonwoven webs.

Absorbent Core

The absorbent core of the present disclosure has a longitudinal direction with a longitudinal axis and perpendicular thereto a lateral direction with a transverse axis. The longitudinal axis is substantially parallel to the longitudinal axis of the disposable diaper and the lateral direction is substantially parallel to the transverse axis of the disposable diaper. The absorbent core further has a front region, a back region and a crotch region therein between and a front lateral edge, an opposing back lateral edge, and longitudinally extending side edges. The absorbent core may comprise a first, lower and a second, upper carrier substrate, and superabsorbent polymer particles placed onto the first carrier substrate or between the first and second carrier substrate. The superabsorbent polymer particles are immobilized by a first core adhesive.

The front zone of the absorbent core represents one third of the absorbent core extending from the front edge of the absorbent core along the longitudinal axis towards the crotch region. The front zone is placed towards the front waist edge of the disposable diaper. The back zone represents one third of the absorbent core extending from the back edge along the longitudinal axis towards the crotch region. The back zone is placed towards the back waist edge of the disposable diaper. The crotch zone represents the remaining third of the absorbent core and extending between the front zone and the back zone. The complete length of the absorbent core is defined as longest extension of the absorbent core along or parallel to the longitudinal axis of the absorbent core. The absorbent core of the present disclosure may be rectangular. In one embodiment, the crotch region of the laminate absorbent core has a narrower width than the front and back regions of the absorbent core, while the front and back edge of the absorbent core still form a straight line.

In one embodiment superabsorbent polymer particles 66 are disposed on the first carrier substrate 64, and the first core adhesive 94 is disposed on the superabsorbent polymer particles 66. Typically the first core adhesive 94 is a hot melt adhesive. In one embodiment the first core adhesive 94 forms a fibrous layer which is at least partially in contact with the superabsorbent polymer particles 66 and partially in contact with the first carrier substrate 64. A second core adhesive (not shown) may be deposited on the first carrier substrate 64 before the application of the superabsorbent polymer particles 66 for enhancing adhesion of the superabsorbent polymer particles 66 and/or of the first core adhesive 94 to the first carrier substrate 64.

The first carrier substrate 64 may be dimensioned such that, after the superabsorbent polymer particles 66 and the first 94 have been applied, the first carrier substrate 64 is folded over onto itself with the superabsorbent polymer particles 66 and the first core adhesive 94 facing inwardly and the first carrier substrate 64 surrounding the superabsorbent polymer particles 66 and the first core adhesive. 94. The area of the first carrier substrate 64, which is folded over, may be free of superabsorbent polymer particles 66 and the first core adhesive 94 prior to being folded over. Alternatively, the area of the first carrier substrate 64, which is folded over, may also comprise superabsorbent polymer particles 66 and a first core adhesive, such that upon folding, the two layers of superabsorbent polymer particles 66 are overlaying each other, with the first core adhesive being sandwiched between the two layers of superabsorbent polymer particles. The superabsorbent polymer particles 66 may be applied in clusters to form land areas 92 and junction areas 96 as is explained below in more detail. Also, the first core adhesive 94 may only be applied to those areas, where the first carrier substrate 64 is folded over. Upon folding, the first core adhesive 94 will also come into contact with the superabsorbent polymer particles 66 of the area, which is not folded over, thus immobilizing the superabsorbent polymer particles 66 of this area.

Alternatively to folding the first carrier substrate 64 over, the absorbent core 14 may also include a second carrier substrate 72. In still another embodiment, the absorbent core may not comprise a second carrier substrate. In this embodiment, the components of the disposable diaper 10 being placed on top of the absorbent core 14 are in direct contact with the superabsorbent polymer particles 66 and the first core adhesive 94.

The first carrier substrate 64, in use of the disposable diaper 10, is facing towards the garment of the wearer and the optional second carrier substrate 72, in use of the disposable diaper, is facing towards the wearer. The optional second carrier substrate 72 may be a nonwoven web or may, alternatively, be a tissue. The first carrier substrate 64 may be a nonwoven web, or may, alternatively be a tissue or a film. The first and second carrier substrate 64, 72 may be made of the same material or they may be made of different material. In embodiments wherein the first and second carrier substrate 64, 72 are both nonwoven webs, these nonwoven webs may be the same nonwoven webs ore they may differ from each other, e.g. with regard to their basis weight, hydrophilicity, air permeability or number and/or type of layers comprised by the nonwoven webs. The type of layers may be spunbonded layers or meltblown layers. The nonwoven webs may also be carded webs made of staple fibers, and the carded webs may or may not comprise binder material. The nonwoven webs may also be hydro-entangled or needle-punched.

The absorbent core 14 may be substantially free of airfelt. The absorbent core 14 typically comprises less than 5% by weight of airfelt, more typically less than 2% by weight and most typically is airfelt free. The absorbent core may not include an acquisition system 50, a topsheet 18, or a backsheet 20 of the disposable diaper 10. In one embodiment, the absorbent core 14 would consist essentially of the first and optional second carrier substrate 64, 72, the superabsorbent polymer particles 66, the first core adhesive 94, and optionally the second core adhesive. "Consist essentially of" in this respect means that these components make up at least 98% by weight of the absorbent core, alternatively at least 99% by weight.

The superabsorbent polymer particles 66 may be substantially continuously distributed within the superabsorbent polymer particles area of the absorbent core 14. "Superabsorbent polymer particle area" as used herein refers to the area (on the wearer facing surface) of the absorbent core which is comprises superabsorbent polymer particles. The areas adjacent the longitudinal side edges and the areas adjacent to the front and back lateral edges of the absorbent core may be free of superabsorbent polymer particles to allow for attaching the edges of the first carrier substrate 64 to the edges of the optional second carrier substrate 72 (or, in the absence of a second carrier substrate 64, the edges of the first carrier substrate may be attached to a layer above the absorbent core 14, such as a layer of the acquisition system 50). Also, the absorbent core 14 may comprise channels, i.e. areas which are substantially free of superabsorbent polymer particles 66 and which are not provided adjacent the edges of the absorbent core 14 but in some other location. "Substantially free of superabsorbent polymer particles", as used herein, means that e.g. due to process-related reasons, a small, negligible amount of superabsorbent polymer particles may be present in the gaps, which however does not contribute to the overall functionality. The term "substantially free of superabsorbent polymer particles" encompasses "free of superabsorbent polymer particles". However, for the present disclosure, the "superabsorbent polymer particle area" comprises at least 80% of the surface area of the absorbent core, alternatively at least 85% or at least 90%.

"Substantially continuously distributed" as used herein means that within the superabsorbent polymer particle area, the first carrier substrate 64 and optional second carrier substrate 72 (or the first substrate and the layer provided on top of the absorbent core 14 towards the wearer, such as a layer of the acquisition system 50) are separated by a multiplicity of superabsorbent polymer particles 66. It is recognized that there may be minor incidental contact areas between the first carrier substrate 64 and second carrier substrate 72 (or the first carrier substrate 64 and the component provided on top of the absorbent core 14 towards the wearer, such as the acquisition system 50) within the superabsorbent polymer particle area. Such incidental contact areas are due to unintentional manufacturing artifacts.

Figure 3:
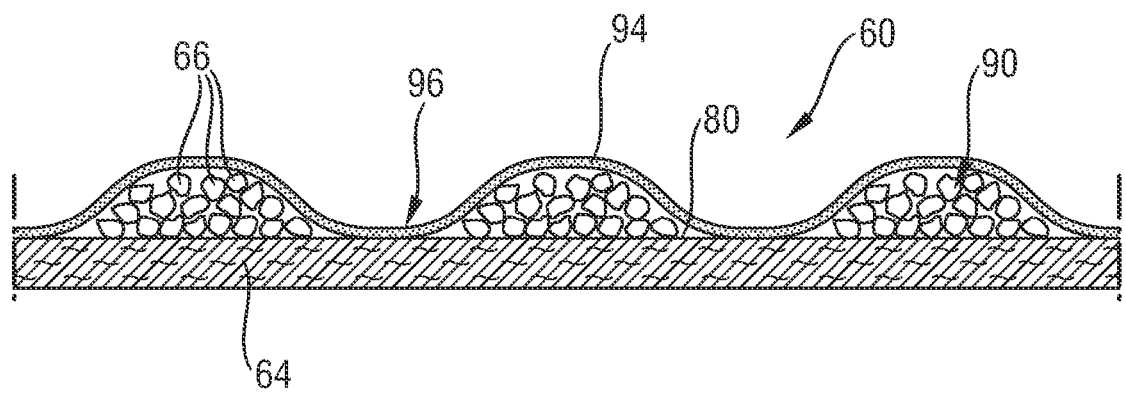
FIG. 3 is a schematic, partial cross sectional view of an absorbent core layer in accordance with an embodiment of the present disclosure.
Figure 4:
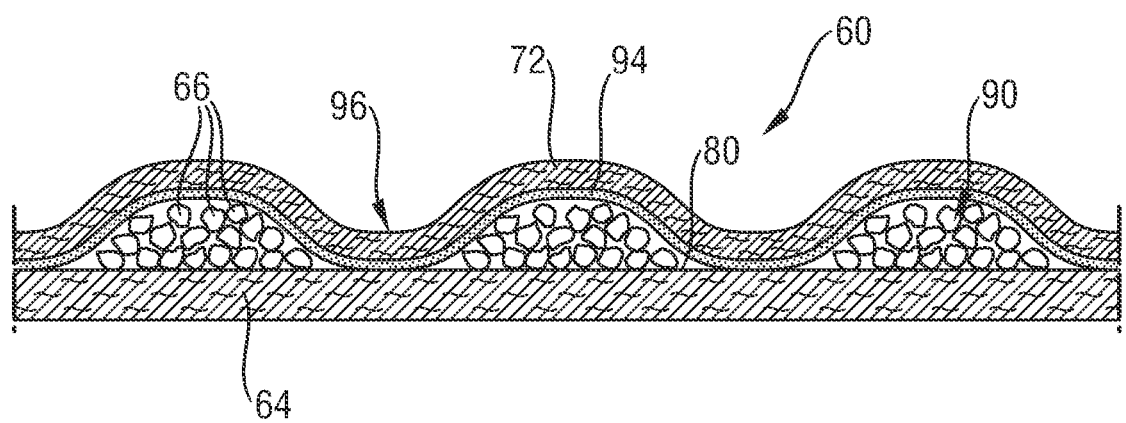
FIG. 4 is a schematic, partial cross sectional view of an absorbent core in accordance with an embodiment of the present disclosure.
Figure 5:
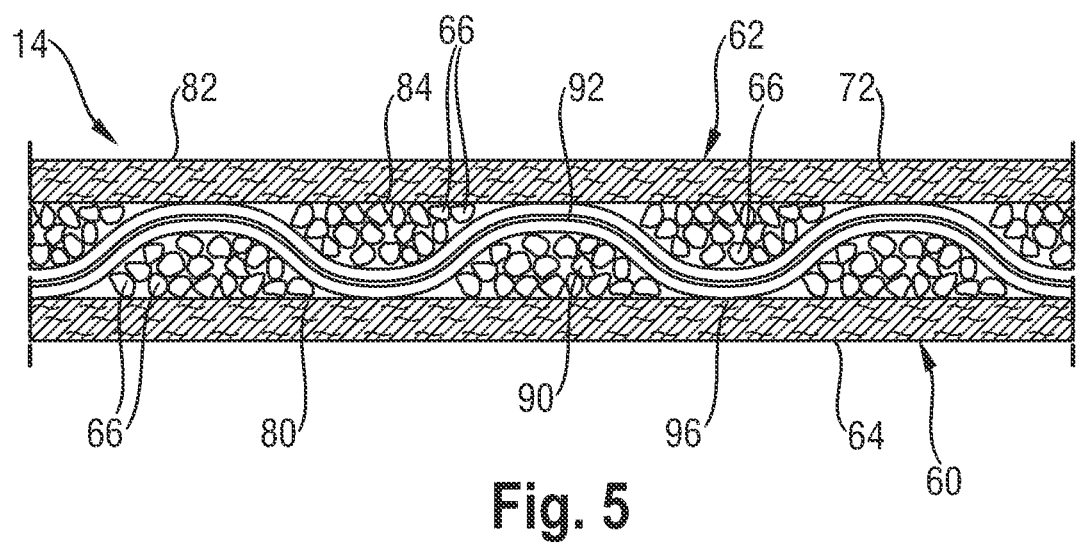
FIG. 5 is a schematic, partial sectional view of an absorbent core in accordance with an embodiment of the present disclosure.

The absorbent core of the present disclosure may comprise—or may consist of—two layers. A first absorbent core layer 60 is shown in FIG. 3. FIG. 4 shows an embodiment of an absorbent core, wherein the first and second absorbent core layer 60, 62 have been combined to form the absorbent core 14. FIG. 5 shows an embodiment of an absorbent core consisting of only one layer In embodiments having a first and a second absorbent core layer, the first absorbent core layer 60 may comprise the first carrier substrate 64 and a first layer of superabsorbent polymer particles 66, wherein the superabsorbent polymer particles 66 are immobilized by a first core adhesive 94. Optionally, the first absorbent core layer 60 may comprise a second core adhesive (not shown). A second core adhesive may be deposited on the first carrier substrate 64 before the application of the superabsorbent polymer particles 66 for enhancing adhesion of the superabsorbent polymer particles 66 and/or of the first core adhesive 94 to the first carrier substrate 64. The first core adhesive 94 may be applied on the superabsorbent polymer particle layer as a fibrous layer, such that a fibrous network is formed.

The second absorbent core layer 62 of such embodiments comprises a second carrier substrate 72 and a second layer of superabsorbent polymer particles 66, wherein the superabsorbent polymer particles 66 may be immobilized by a first core adhesive 94. Optionally, the second absorbent core layer 62 may comprise a second core adhesive (not shown). A second core adhesive may be deposited on the second carrier substrate 72 before the application of the superabsorbent polymer particles 66 for enhancing adhesion of the superabsorbent polymer particles 66 and/or of the first core adhesive 94 to the second carrier substrate 72. The first core adhesive 94 may be applied on the superabsorbent polymer particle layer as a fibrous layer, such that a fibrous network is formed.

Once the first and second absorbent core layer 60, 62 is formed, the two absorbent core layers are combined with their respective carrier substrates 64, 72 facing outwardly and sandwiching the superabsorbent polymer particles 66 between them to form the absorbent core 14.

In one embodiment, a further substrate (not shown), such as a tissue or nonwoven web is positioned in between the first and second absorbent core layer. However, it is desired that no such substrates are positioned between the first and second absorbent core layer and that the first layer of superabsorbent polymer particles is separated from the second layer of superabsorbent polymer particles only the a fibrous layer of first core adhesive.

FIG. 3 shows a single absorbent core layer. The superabsorbent polymer particles 66 are deposited on the first carrier substrate 64 in clusters 90 of particles comprising land areas 92 and junction areas 96 between the land areas 94. In the land areas 94, the first core adhesive 94 may not contact the first carrier substrate 64 or the optional second core adhesive directly; junction areas 96 are areas where the first core adhesive 94 contacts the first carrier substrate 64 or the optional second core adhesive directly. The junction areas 96 contain little or no superabsorbent polymer material 66. The land areas 94 and junction areas 96 can have a variety of shapes including, but not limited to, circular, oval, square, rectangular, triangular, and the like.

By applying the first core adhesive 94 as a fibrous layer, the first core adhesive 94 entangles the superabsorbent polymer particles 66, and thereby immobilizes the particles. In a further aspect, the first core adhesive 94 bonds to the carrier substrate 64 and thus affixes the superabsorbent polymer particles 66 to the carrier substrate 64. In another embodiment, the first core adhesive 68 may also penetrate to a certain extent into the carrier substrate 64, thus providing for further immobilization and affixation.

As already explained above, the first and second carrier substrates 64 and 72 may be adhered to one another with adhesive about the periphery to form an envelope about the superabsorbent polymer particles 66 to hold the superabsorbent polymer particles 66 within the absorbent core 14.

As best seen in FIG. 4, the first and second absorbent core layers 60 and 62 are combined to form the absorbent core 14.

The first and second absorbent core layers 60 and 62 may be combined together to form the absorbent core 14 with the absorbent core layers being offset such that the superabsorbent polymer particles 66 on the first carrier substrate 64 and the superabsorbent polymer particles 66 on the second carrier substrate 72 taken in combination are substantially continuously distributed across the superabsorbent polymer particle area. In a certain embodiment, the superabsorbent polymer particles 66 are substantially continuously distributed across the superabsorbent polymer particle area while the superabsorbent polymer particles 66 of the respective first and second absorbent core layer alone are discontinuously distributed across the first and second carrier substrates 64 and 72 in clusters 90. In a certain embodiment, the absorbent core layers may be offset such that the land areas 92 of the first absorbent core layer 60 face the junction areas 96 of the second absorbent core layer 62 and the land areas 92 of the second absorbent core layer 62 face the junction areas 96 of the first absorbent core layer 60. When the land areas 92 and junction areas 96 are appropriately sized and arranged, the resulting combination of superabsorbent polymer particles 66 are a substantially continuous layer of superabsorbent polymer particles across the superabsorbent polymer particle area of the absorbent core 14.

According to the present disclosure, the superabsorbent polymer particles is typically present in an amount greater than about 85% by weight of the absorbent core, or greater than about 90% by weight of the absorbent core, or greater than about 95% by weight of the absorbent core. Also, the superabsorbent polymer particles may present more than 95% of the absorbent material comprised by the absorbent core. The absorbent core may comprise less than 5% of airfelt (i.e. cellulose fibers). Typical absorbent materials are superabsorbent polymer particles, airfelt (i.e. cellulose fibers) and—less frequently used—absorbent foams. Typically, the absorbent core comprises from 50 g/m$^2$ to 2200 g/m$^2$ of the superabsorbent polymer particles, from 100 g/m$^2$ to 1500 g/m$^2$ or even from 200 g/m$^2$ to 1200 g/m$^2$.

According to the present disclosure, the amount of superabsorbent polymer particles may or may not vary along the length of the absorbent core, typically the absorbent core being profiled in its longitudinal direction. It has been found that, for disposable diapers, the liquid discharge occurs predominately in the front half of the disposable diaper. The front half of the absorbent core 14 should therefore comprise most of the absorbent capacity of the absorbent core. Thus, the front half of the absorbent core 14 may comprise more than about 60% by weight of the total amount of superabsorbent polymer particles comprised by the absorbent core, or more than about 65% by weight, 70% by weight, 75% by weight, 80% by weight, 85% by weight, or 90% by weight of the superabsorbent polymer particles.

Typically the first core adhesive may serve to at least partially immobilize the superabsorbent polymer particles both in dry and wet state. The first core adhesive can be disposed essentially uniformly within the absorbent particulate polymer particles between the superabsorbent polymer particles. However, typically the first core adhesive 94 may be provided as a fibrous layer which is at least partially in contact with the superabsorbent polymer particles 66 and partially in contact with the first carrier substrate 64 and—if present—the optional second carrier substrate 72. Typically, the first core adhesive 94 forms a fibrous network over the superabsorbent polymer particles 66 of each absorbent core layer. As for example illustrated in FIG. 4, the superabsorbent polymer particles 66 may be provided as a discontinuous layer, and a layer of first core adhesive 94 is laid down onto the layer of superabsorbent polymer particles 66 and 74, such that the first core adhesive 94 is in direct contact with the superabsorbent polymer particles 66, but also in direct contact with the surfaces 80 and 84 of the carrier substrates 64 and 72 facing towards the superabsorbent polymer particles 66 of the absorbent core 14, in locations where the carrier substrates 64, 72 are not covered by the superabsorbent polymer particles 66. This imparts an essentially three-dimensional structure to the fibrous layer of first core adhesive 94, which in itself is essentially a two-dimensional structure of relatively small thickness, as compared to the dimension in length and width directions. In other words, the first core adhesive 94 undulates between the superabsorbent polymer particles 66 and the surfaces 80, 84 of the carrier substrates 64 and 72 facing towards the superabsorbent polymer particles of the absorbent core 14.

The first core adhesive may 94 provide cavities to cover the superabsorbent polymer particles, and thereby immobilizes this material. In a further aspect, the first core adhesive bonds to the carrier substrate(s) and thus affixes the superabsorbent polymer particles to the carrier substrate(s). Of course, while the first core adhesives disclosed herein provide an improved wet immobilization (i.e., immobilization of superabsorbent polymer particles when the disposable diaper and thus the absorbent core at least partially is wetted), these first core adhesives may also provide a good immobilization of superabsorbent polymer particles when the absorbent core is dry.

Superabsorbent Polymer Particles

The superabsorbent polymer particles may be of numerous shapes. The term "particles" refers to granules, fibers, flakes, spheres, powders, platelets and other shapes and forms known to persons skilled in the art of superabsorbent polymer particles. E.g. the particles can be in the form of granules or beads, having a particle size from about 10 μm to about 1000 μm, alternatively from about 100 μm to about 1000 μm, alternatively from about 150 μm to about 850 μm and alternatively from about 150 μm to about 500 μm. In another embodiment, the superabsorbent polymer particles can be in the shape of fibers, i.e. elongated, acicular superabsorbent polymer particles. In those embodiments, the superabsorbent polymer fibers have a minor dimension (i.e. diameter of the fiber) of less than about 1 mm, usually less than about 500 μm, and alternatively less than 250 μm down to 50 μm. The length of the fibers may be about 3 mm to about 100 mm. The fibers can also be in the form of a long filament that can be woven.

Some superabsorbent polymer particles of the present disclosure are spherical-like particles. According to the present disclosure and in contrast to fibers, "spherical-like particles" have a longest and a smallest dimension with a particulate ratio of longest to smallest particle dimension in the range of 1-5, where a value of 1 would equate a perfectly spherical particle and 5 would allow for some deviation from such a spherical particle.

The superabsorbent polymer particle materials useful in the present disclosure include a variety of water-insoluble, but water-swellable polymers capable of absorbing large quantities of fluids. Such polymers materials are generally known in the art and include all those well-known polymers used or deemed useful in the context of disposable absorbent article technology.

Example polymer materials for use in making superabsorbent polymer particles are slightly network cross linked polymers of partially neutralized polyacrylic acids and starch derivatives thereof. Starch-based superabsorbent polymer particles are also encompassed in the present disclosure. The superabsorbent polymer particles may comprise from 25% to 95% by weight, alternatively from 50% to 80% by weight neutralized, slightly network cross-linked, polyacrylic acid. Network cross-linking renders the polymer substantially water-insoluble and, in part, determines the absorptive capacity and extractable polymer content characteristics of the superabsorbent polymer particles.

While the superabsorbent polymer particles may be of one type (i.e., homogeneous), mixtures of polymers can also be used in the present disclosure. The superabsorbent polymer particles can also comprise mixtures with low levels of one or more additives, such as for example powdered silica, surfactants, adhesive, binders, and the like. Furthermore, the superabsorbent polymer particles can comprise a gradient in particle size or can comprise a certain range of particle size.

Many of the formerly known superabsorbent polymer particles exhibited gel blocking "Gel blocking" occurs when particles made of the superabsorbent polymer materials are wetted and the particles swell so as to inhibit fluid transmission to other zones or regions of the absorbent structure. Wetting of these other regions of the absorbent core therefore takes place via a very slow diffusion process. In practical terms, this means acquisition of fluids by the absorbent structure is much slower than the rate at which fluids are discharged, especially in gush situations. Leakage from the disposable diaper can take place well before the superabsorbent polymer particles in the absorbent core are even close to being fully saturated or before the fluid can diffuse or wick past the "blocking" particles into the rest of the absorbent core.

One commonly applied way to reduce gel blocking is to make the particles stiffer, which enables the superabsorbent polymer particles to retain their original shape thus creating or maintaining void spaces between the particles. A well-known method to increase stiffness is to covalently and/or ionically cross-link the carboxyl groups exposed on the surface of the superabsorbent polymer particles. This method is commonly referred to as surface cross-linking First and Second Core Adhesive The first and optional second core adhesive comprised by the absorbent core may be a hot melt adhesive. In certain embodiments, the first core adhesive is a hot melt adhesive whereas the second core adhesive may be another type of adhesive. The average basis weight of first plus optional second core adhesive in the absorbent core may be from 0.5 $g/m^2$ to 30 $g/m^2$, between 1 $g/m^2$ to 15 $g/m^2$, between 1 $g/m^2$ and 10 $g/m^2$ or even between 1.5 $g/m^2$ and 5 $g/m^2$.

The first core adhesive serves to at least partially immobilize the superabsorbent polymer particles of the absorbent core, both in dry and wet condition.

Without wishing to be bound by theory, it has been found that those hot melt adhesives which are most useful for immobilizing the superabsorbent polymer particles combine good cohesion and good adhesion behavior. Good adhesion may promote good contact between the hot melt adhesive and the superabsorbent polymer particles and the carrier substrates. Good cohesion reduces the likelihood that the adhesive breaks, in particular in response to external forces, and namely in response to strain. When the absorbent core absorbs liquid, the superabsorbent polymer particles swells and subjects the hot melt adhesive to external forces. The hot melt adhesive may allow for such swelling, without breaking and without imparting too many compressive forces, which would restrain the absorbent particulate polymer particles from swelling.

In accordance with present disclosure the hot melt adhesive may comprise, in its entirety, a single thermoplastic polymer or a blend of thermoplastic polymers, having a softening point, as determined by the ASTM Method D-36-95 "Ring and Ball", in the range between 50° C. and 300° C., or alternatively the hot melt adhesive may comprise at least one thermoplastic polymer in combination with other thermoplastic diluents such as tackifying resins, plasticizers and additives such as antioxidants.

In certain embodiments, the thermoplastic polymer typically has a weight average molecular weight (Mw) of more than 10,000 and a glass transition temperature ($T_g$) usually below room temperature (25° C.), or of less than 22° C., or less than 18° C., or less than 15° C. In certain embodiments $T_g$ may be above 0° C.>$T_g$. In embodiments where the thermoplastic polymer has more than one $T_g$ the values given refer to the lowest glass transition temperature. The thermoplastic polymer may also have a softening point, as determined by the ASTM Method D-36-95 "Ring and Ball", in the range between 50° C. and 300° C. In some embodiments the Mw of the thermoplastic polymer is less than 10000000.

In certain embodiments, typical concentrations of the thermoplastic polymer in a hot melt adhesive are in the range of about 20% to about 40% by weight of the hot melt adhesive.

Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof.

Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of $C_2$ to $C_8$ alpha olefins.

In exemplary embodiments, the tackifying resin has typically a Mw below 5,000 and a $T_g$ usually above room temperature (25° C.), typical concentrations of the tackifying resin in a hot melt are in the range of about 30% to about 60% by weight of the hot melt adhesive. In certain embodiments the tackifying resin has an Mw of more than 1,000.

The plasticizer has a low Mw of typically less than 1,000 and a $T_g$ below room temperature, with a typical concentration of about 0% to about 15% by weight of the hot melt adhesive. In certain embodiments the plasticizer has an Mw of more than 100.

In certain embodiments, the first and/or second core adhesive is hot melt adhesive present in the form of fibers. In some embodiments, the fibers will have an average thickness of about 1 to about 50 micrometers or about 1 to about 35 micrometers and an average length of about 5 mm to about 50 mm or about 5 mm to about 30 mm.

The absorbent core may also comprise a second core adhesive which is not illustrated in the figures. The second core adhesive may be deposited on the carrier substrate before application of the superabsorbent polymer particles on the carrier substrate for enhancing adhesion of the superabsorbent polymer particles and the first core adhesive to the respective carrier substrate. The second core adhesive may also aid in immobilizing the superabsorbent polymer particles and may be the same adhesive as the first core adhesive or may be different from the first core adhesive. The second core adhesive may also be a hot melt adhesive. An example of commercially available second core adhesive is H.B. Fuller Co. (St. Paul, Minn.) Product No. HL-1620-B. The second core adhesive may be applied to the carrier substrate(s) by any suitable means, but according to certain embodiments, may be applied in about 0.5 to about 1 mm wide slots spaced about 0.5 to about 2 mm apart.

Attachment of Absorbent Core to Backsheet

If a disposable diaper is applied onto a wearer, the disposable diaper will take a curved shape in order to conform to the wearer (i.e. the diaper will not be flattened out but will be bent with the front and back waist regions of the diaper lying against the waist of the wearer and the crotch region of the diaper being placed against the crotch region of the wearer). Moreover, the diaper is subjected to a certain degree of bending along lines which are substantially parallel to the longitudinal axis of the diaper between the wearer legs and towards the front waist region. Such bending results in buckling of the diaper, i.e. the diaper is bulged outwardly in the crotch region and in at least parts of the front waist region.

Upon applying the disposable diaper onto a wearer by bending it, the surface areas of the disposable diaper is altered as follows versus a flattened out diaper: While the upper, wearer-facing surface (i.e. the topsheet) is upset and upended, the lower, garment-facing surface (i.e. the backsheet) is elongated. The same applies for the absorbent core within the disposable diaper: The upper, wearer-facing surface (such as the second, upper carrier substrate) is upset and upended while the lower, garment-facing surface (such as the first, lower carrier substrate) is elongated.

In the vast majority of disposable diapers on the market today, the absorbent core comprises a considerable amount of cellulose fibers (airfelt). The superabsorbent polymer particles comprised in these absorbent cores are mixed with the cellulose fibers and the particles are thus held in place in the interstices between the cellulose fibers. Generally, no adhesive is used to immobilize the superabsorbent polymer particles. Overall, these absorbent cores have a rather plastic characteristic. If such diapers undergo the bending described above when the disposable diaper is applied onto a wearer, the material within the absorbent core is able to compensate at least some of the upending of the upper surface and the elongation of the lower surface by migration of cellulose fibers and superabsorbent polymer particles within the core.

Also, when the disposable diaper gets wetted and the superabsorbent polymer particles swell and expand, the superabsorbent polymer particles can to a certain extent swell within the interstices of the cellulose fibers. Hence, the volume increase of the absorbent core as a whole is less than the volume increase of the superabsorbent polymer particles because the dry absorbent core provides some free space into which the particles can expand.

In an absorbent core of the present disclosure, which comprises little or no airfelt and wherein the superabsorbent polymer particles are immobilized by an adhesive, the absorbent core has a much more elastic characteristic compared to the conventional absorbent core described above. As the superabsorbent polymer particles are immobilized much stronger than superabsorbent polymer particles which are simply mixed within a cellulose fiber matrix, the superabsorbent polymer particles cannot migrate within the absorbent core when the disposable diaper is applied onto a wearer. Therefore, the buckling of the upper, wearer-facing surface as well as the elongation of the lower, garment-facing surface is much more pronounced as in conventional, airfelt-containing disposable diapers.

Also, as the disposable diaper is wetted, the superabsorbent polymer particles swell and expand. Contrary to a conventional, airfelt-containing absorbent core, an absorbent core having little or no airfelt may not provide any "free space" in the interstices between the cellulose fibers, into which the superabsorbent polymer particles can expand. Thus, the absorbent core as a whole will expand and swell much earlier (i.e. much longer before the absorption capacity limit of the absorbent core is reached) and will expand much more compared to a conventional absorbent core. Such expansion increases the strain applied onto the lower, garment-facing surface (such as the lower carrier substrate) of the absorbent core and, in turn, increases the strain applied onto the backsheet. Consequently, the lower, garment-facing surface of the absorbent core as well as the backsheet will elongate further upon wetting of the diaper.

As a consequence of the elongation of the wearer-facing surface, the absorbent core is firmly pressed against the backsheet of the disposable diaper. Upon absorption of urine and runny feces, the absorbent core is stained and, due to the dense contact between the absorbent core and the backsheet, the staining may be visible through the backsheet, especially if the basis weight of the backsheet material is low and/or if the backsheet has a little or no printing. This see-through of stains has a negative impact on consumer acceptance of the disposable diaper, as it is perceived as low quality. Moreover, the see-through is often interpreted as indicating wet-through, i.e. the absorbent core is perceived as being soaked with liquid, signaling that the absorbent core has reached its capacity maximum—even if in fact the diaper is far from reaching its maximum capacity. Also the backsheet may be perceived as being wet upon visual inspection of the disposable diaper.

Furthermore, upon elongation and straining of the backsheet, the backsheet tends to buckle and form wrinkles and tension lines. These tension lines and wrinkles are interpreted by consumers as signals that the absorbent capacity of the disposable diaper is exhausted and the diaper needs to be changed. This effect may occur long before the actual capacity limit of the diaper is reached.

The inventors have found that the above explained disadvantages can be reduced if the attachment of absorbent core to backsheet is altered: In conventional, airfelt-containing disposable diapers as well as in commercially available disposable diapers having little or no airfelt (e.g. Pampers "Active Fit" sold in Germany in May 2011), the absorbent core is adhesively attached to the backsheet over the complete garment-facing surface of the absorbent core (hence, e.g. the first carrier substrate of the absorbent core). This does not necessarily mean that 100% of the surface area of the carrier substrate are covered with adhesive but it may be that the adhesive, such as hot melt adhesive, is applied in small spirals and these spirals are applied all over the carrier substrate.

If the absorbent core is adhesively attached to the backsheet over essentially the whole area of the absorbent core, the absorbent core cannot move and expand independently from the backsheet. Consequently, as the absorbent core expands upon swelling of the superabsorbent polymer particles, the backsheet will also have to expand.

It has been found that this drawback can be reduced if the absorbent core is not attached to the backsheet over the whole absorbent core surface. If the absorbent core is attached to the backsheet only in certain, limited areas, and if these areas are carefully and meaningfully chosen, the formation of buckles and wrinkles in the backsheet can be reduced. Also, see-through of urine stains from the absorbent core through the backsheet can be reduced.

According to the present disclosure, the absorbent core is attached to the backsheet in any of the following locations:

a) The absorbent core is attached to the backsheet of the disposable diaper in attachment zones adjacent to the front lateral edge and the back lateral edge of the absorbent core and the absorbent core is unattached to the backsheet in any other region; or b) the absorbent core is attached to the backsheet of the disposable diaper in the crotch region of the absorbent core in one or more attachment zone(s) on or adjacent to the longitudinal axis of the absorbent core, wherein the one or more attachment zone(s) cover from 0.2% to 3% of the total surface area of the absorbent core, and the absorbent core is unattached to the backsheet in any other region; or c) the absorbent core is attached to the backsheet of the disposable diaper in the crotch region of the absorbent core in attachment zones adjacent to the longitudinal side edges of the absorbent core and the absorbent core is unattached to the backsheet in any other region; or d) the absorbent core is attached to the backsheet of the disposable diaper in combinations of any of the attachment zones defined in a) to c) and the absorbent core is unattached to the backsheet in any other region.

If the absorbent core is attached to the backsheet according to option a), the attachment zones adjacent the front lateral edge and the back lateral edge of the absorbent core may be provided only in the corners of the absorbent core, leaving the remaining area adjacent the front lateral edge and the back lateral edge of the absorbent core unattached to the backsheet. The "remaining area" refers to 70%, or 80% of the width of the absorbent core in the area adjacent to the front and back lateral edges. The one or more attachment zone(s) of option a) or d) may cover from 0.2% to 3%, alternatively from 0.5% to 2%, or from 0.5% to 1.5%, or from 0.2% to 1.5% or from 0.2% to 1% of the total surface area of the absorbent core. These percentages refer to the totality of all attachment zones taken together.

In embodiments according to option a), the absorbent core may be attached to the backsheet in one attachment zone adjacent to the front lateral edge and in one attachment zone adjacent to the back lateral edge of the absorbent core and may be unattached to the backsheet in any other region. Alternatively, the absorbent core may be attached to the backsheet in two, three or more attachment zones adjacent to the front lateral edge and in two, three or more attachment zones adjacent to the back lateral edge of the absorbent core and may be unattached to the backsheet in any other region. In still another alternative, the absorbent core may be attached to the backsheet in one attachment zone adjacent to the front lateral edge of the absorbent core and in two, three or more attachment zones adjacent to the back lateral edge and be unattached to the backsheet in any other region; or may be attached to the backsheet in two, three or more attachment zones adjacent to the front lateral edge of the absorbent core and in one attachment zone adjacent to the back lateral edge and be unattached to the backsheet in any other region.

In embodiments according to option c), the absorbent core may be attached to the backsheet in one attachment zone adjacent to one longitudinal side edge and in one attachment zone adjacent to the respective other longitudinal side edge and may be unattached to the backsheet in any other region. Alternatively, the absorbent core may be attached to the backsheet in two, three or more attachment zones adjacent to one longitudinal side edge and in two, three or more attachment zones adjacent to the respective other longitudinal side edge of the absorbent core and may be unattached to the backsheet in any other region. In still another alternative, the absorbent core may be attached to the backsheet in one attachment zone adjacent to one longitudinal side edge of the absorbent core and in two, three or more attachment zones adjacent to the respective other longitudinal side edge and be unattached to the backsheet in any other region.

If the absorbent core is attached to the backsheet according to option b), the one or more attachment zone(s) in the crotch region may have a longitudinal direction substantially parallel to the longitudinal direction of the absorbent core and may have a lateral direction substantially parallel to the lateral direction of the absorbent core. The ratio between longitudinal direction and lateral direction of the one or more attachment zone(s) may be from 0.5 to 2.0, or from 2.0 to 0.5, or from 0.5 to 1.0, or from 1.0 to 0.5. The one or more attachment zone(s) of option b) cover from 0.2% to 3%, alternatively from 0.5% to 2%, or from 0.5% to 1.5%, or from 0.2% to 1.5% or from 0.2% to 1% of the total surface area of the absorbent core. These percentages refer to the totality of all attachment zones taken together. Also, if the absorbent core is attached to the backsheet according to option b), the disposable diaper may further comprise a wetness indicator with the wetness indicator being placed between the absorbent core and the backsheet in at least one of the one or more attachment zone(s) in the crotch region of the absorbent core on or adjacent to the longitudinal axis of the absorbent core.

The term "adjacent to the front lateral edge and the back lateral edge of the absorbent core", as used herein, means a distance of less than 15%, or less than 10%, or less than 5% (based on the total length of the absorbent core) inwardly, starting from the front lateral edge (for attachment zone(s) adjacent to the front lateral edge) and back lateral edge (for attachment zone(s) adjacent to the back lateral edge), respectively, and extending along or parallel to the longitudinal axis of the absorbent core towards the crotch zone.

The term "adjacent to the longitudinal axis of the absorbent core", as used herein, means that the attachment zone is either on the longitudinal axis or is at a distance of less than 15%, or less than 10%, or less than 5% (based on the total width of the absorbent core) away from the longitudinal axis towards the left or right longitudinal side edge. For embodiments having more than one attachment zone adjacent to the longitudinal axis of the absorbent core, the attachment zones may be at a distance of less than 15%, or less than 10%, or less than 5% (based on the total width of the absorbent core) away from the longitudinal axis towards the left and right longitudinal side edge.

The term "adjacent to the longitudinal side edges of the absorbent core" as used herein, means a distance of less than 15%, or less than 10%, or less than 5% (based on the total width of the absorbent core) inwardly, starting from the left and right longitudinal edge, respectively, and extending along or parallel to the transverse axis of the absorbent core towards the crotch zone.

The total surface area of the absorbent core is defined by the x- and y-dimension of the absorbent core. Any potential unevenness of the surface and irregularities of thickness (i.e. in the z-direction) is not taken into account. The x-,y-dimension of the absorbent core is determined while the absorbent core is lying flat on a table with not stress or strain applied (this also applies for potentially extensible absorbent cores). If needed, elastically contracting elements that otherwise would apply strain to the absorbent core can be carefully removed prior to lying the absorbent core flat on a table.

Attaching the absorbent core to the backsheet according to any of options a) to d) above, the absorbent core, while expanding upon liquid absorption, may slide relative to the backsheet, thus the absorbent core may expand largely independently from the backsheet and not forcing the backsheet to expand together with the absorbent core. Hence, the formation of wrinkles and tension lines in the backsheet can be reduced. Also, see-through of urine strains through the backsheet can be reduced (as the absorbent core is not held as closely against the backsheet as in embodiments where the absorbent core is attached to the backsheet over the whole absorbent core area). This is believed to be due to the formation of a small air-cushion between the absorbent core and the backsheet, which cannot be formed in areas, where the absorbent core is closely attached (e.g. by adhesive) to the backsheet. To reduce see-through, a very small air-cushion is believed to be sufficient. For visualizing the reduction of see-through, the test method set out below can be used. This test method allows a qualitative visualization with the naked eye (i.e. without the need for microscope or the like).

In the disposable diapers of the present disclosure, the topsheet may be sealed to the backsheet along the perimeter of the topsheet and backsheet, i.e. outside the areas, where the absorbent core is encased between the topsheet and backsheet. To allow the absorbent core to expand between the topsheet and backsheet, the topsheet may be sealed to the backsheet at a distance away from the perimeter of the absorbent core, especially in the transverse direction, i.e. along the longitudinal side edges of the absorbent core. The seal between the topsheet and the backsheet along the longitudinal side edges of the absorbent core may be such, that the width of the absorbent core is less than 90%, alternatively less than 85% of the width between the longitudinal side edge seals between the topsheet and the backsheet. If the width of the absorbent core and/or the width between the longitudinal side edge seals between the topsheet and the backsheet varies along the length of the disposable diaper, the width of the absorbent core may be less than 90%, alternatively less than 85% of the width between the longitudinal side edge seals between the topsheet and the backsheet at every location along the length of the disposable diaper.

Attaching the absorbent core to the backsheet in attachment zones adjacent to the front lateral edge and the back lateral edge of the absorbent core or in attachment zones adjacent to the longitudinal side edges of the absorbent core has the benefit, that the absorbent core cannot twist or even roll over in the disposable diaper, as it is held in place in more than one location. This is especially advantageous for certain manufacturing processes, where individual absorbent cores are placed onto an endless web of backsheet material (which is cut into individual backsheets only at a later stage in the manufacturing process). The topsheet is placed on top of the absorbent core only after the absorbent core has been placed onto the endless backsheet material, typically in form of an endless web of topsheet material, which is cut into individual topsheets at a later stage together with the backsheet. Hence, at a certain stage, the absorbent core is lying on top of the backsheet with no overlying components. The absorbent core, besides being attached to the endless web of backsheet material in the attachment zones, is typically held onto the backsheet by a vacuum, which is underneath the backsheet. However, at this stage, there is a risk that the absorbent core lifts from the backsheet especially in high speed manufacturing processes. Thus, attaching the absorbent core to the backsheet in more than one attachment zone, as is the case in option a), c) and d) set out above, bears a reduced risk of absorbent core lift up versus option b), wherein the absorbent core is attached to the backsheet only in one location.

However, attaching the absorbent core to the backsheet only in one location is nevertheless possible, if the manufacturing process is adapted accordingly (i.e. higher vacuum, slower speed of manufacturing line, or joining the absorbent core and the topsheet onto the backsheet at the same time). Attaching the absorbent core to the backsheet according to option b), i.e. only in one attachment zone has the advantage that expansion of the wetted absorbent core is not hindered both parallel to the longitudinal axis and parallel to the transverse axis of the absorbent core. Once the topsheet has been placed on top of the absorbent core, the topsheet can be sealed to the backsheet around the perimeter of the topsheet and backsheet, which can be done prior to or after cutting the endless topsheet and backsheet material into individual topsheets and backsheets. Also, the topsheet may be attached to the absorbent core once the topsheet has been put onto the absorbent core.

As see-through is reduced, the present disclosure allow using low basis weight backsheet materials. The backsheet of the disposable diaper of the present disclosure may consist of a film and optionally one or more nonwoven webs. The basis weight of the backsheet including film and optional nonwoven webs may be less than 70 $g/m^2$, or may be from 25 $g/m^2$ to 70 $g/m^2$, or from 25 $g/m^2$ to 60 $g/m^2$ or from 25 $g/m^2$ to 50 $g/m^2$. The film (without nonwoven webs) may have a basis weight of less than 25 $g/m^2$, or from 10 $g/m^2$ to 25 $g/m^2$, or from 10 $g/m^2$ to 20 $g/m^2$. The optional nonwoven webs may have a basis weight of less than 40 $g/m^2$, or from 10 $g/m^2$ to 30 $g/m^2$, or from 10 $g/m^2$ to 25 $g/m^2$ (in embodiments having more than one nonwoven web, these values represent the sum for all nonwoven webs taken together).

Also, according to the present disclosure, the backsheet may be white and may have a printed area (with non-white colors) of less than 50%, or less than 30% in the area which is coincident with the front region and crotch region of the absorbent core.

The backsheet of the disposable diaper of the present disclosure may not be elastic. Non-elastic materials are generally less expensive compared to elastic materials and given that the absorbent core is able to expand independently from the backsheet to some extent, it is not necessary that the backsheet is elastic. Hence, the backsheet of the present disclosure may be non-elastic or highly non-elastic.

The absorbent core may be attached to the topsheet of the disposable diaper. As the topsheet is typically only attached to the backsheet at the perimeter of the topsheet and backsheet, such attachment to the topsheet will not adversely affect the advantages of the present disclosure, namely reduced see-through and reduced formation of wrinkles and tension lines in the backsheet. The absorbent core may be attached to the topsheet at least in the front region and in the crotch region of the absorbent core. The absorbent core may be directly attached to the topsheet. Alternatively, in disposable diapers having an acquisition system between the topsheet and the absorbent core, the absorbent core may be attached to the acquisition system, which in turn is attached to the topsheet. Attachment of absorbent core to the topsheet or acquisition system may be done adhesively, for example using hot melt adhesive.

Attachment of the absorbent core to the backsheet according to the present disclosure may be done with adhesive, optionally a hot melt adhesive. The attachment is directly between the absorbent core and the backsheet. If the absorbent core has a first carrier substrate, the attachment is between the garment-facing surface of the lower carrier substrate and the wearer-facing surface of the backsheet.

The absorbent core of the present disclosure may comprise one or more channels, i.e. areas which are substantially free of superabsorbent polymer particles and which are not provided adjacent the edges of the absorbent core but in some other location. "Substantially free of superabsorbent polymer particles", as used herein, means that e.g. due to process-related reasons, a small, negligible amount of superabsorbent polymer particles may be present in the gaps, which however does not contribute to the overall functionality. The term "substantially free of superabsorbent polymer particles" encompasses "free of superabsorbent polymer particles". The channels may be provided in the crotch region and/or in the front region of the absorbent core. The channels are elongated and may have a width to length ratio of 1 to 20, or 1 to 15, or 1 to 10, or 1 to 5, or 1 to 3. The channels may be straight or may be curved. Such channels can further help to improve the conformity of the disposable diaper, i.e. the diaper conforms better to the wearer. This can further help to reduce the tension lines and wrinkles of the backsheet discussed above. If the absorbent core comprises one or more channels, the attachment zones, where the absorbent core is attached to the backsheet, may be outside the area(s) which is (are) provided with the one or more channels. The channels may not extend onto the front and back lateral edges and longitudinal edges of the absorbent core.

The absorbent core of the present disclosure may further have a first carrier substrate, which is the substrate of the absorbent core that is lying directly on top of the backsheet. If the absorbent core comprises one or more channels, first carrier substrate may be water permeable (at 25° C. and 50% RH) (such as a tissue web or a water permeable nonwoven web). In such embodiments, a certain amount of liquid (urine) may penetrate through the complete thickness of the absorbent core and may be distributed in the space between the absorbent core and the backsheet. Thus, liquid distribution may be improved, as the liquid may spread between the absorbent core and the backsheet to other, more remote areas where it can be absorbed by the absorbent core. Taken in combination with the attachment zones of the present disclosure, where the absorbent core is attached to the backsheet and is left unattached to the backsheet in any other region, the liquid between the absorbent core and the backsheet can spread relatively unobstructed. However, in these absorbent cores, the size of the one or more channels has to be chosen carefully to ensure that the amount of liquid passing through the thickness of the absorbent core in the space between the absorbent core and the backsheet does not become too extensive.

Test Method to Visualize Backsheet See-Through

This method visualizes the see-through of stains through the backsheet of a disposable diaper. The test can be carried out with disposable diapers having different pattern and extent absorbent core attachment to backsheet to qualitatively visualize the differences. The load protocol used is for disposable diapers typically designated for wearers having a weight in the range of 8 to 13 kg±20% (such as Pampers "Active Fit", Size 4 or other Pampers baby diapers Size 4, Huggies baby diapers Size 4 and baby diapers Size 4 of most other tradenames).

Apparatus Load Protocol

Figure 6:
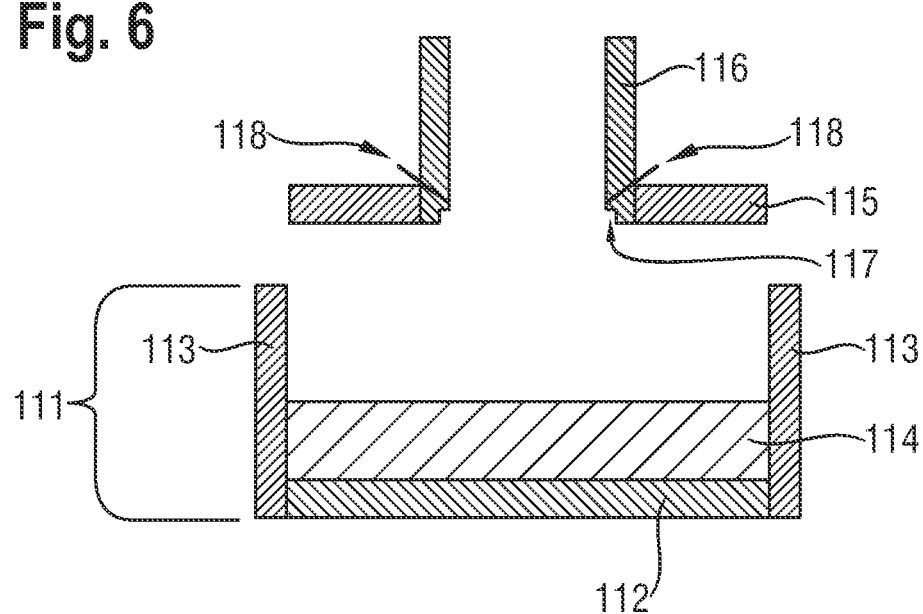
FIG. 6 is a schematic, cross-sectional view of a suitable system for conducting the test method to visualize backsheet see-through in accordance with an embodiment of the present disclosure.

The test apparatus is shown in FIG. 6 and comprises a trough 111 made of polycarbonate (e.g. Lexan®) nominally 12.5 mm (0.5 inch) in thickness. The trough 111 comprises a rectilinear horizontal base 112 having a length of 508 mm (20.0 inches), and a width of 152 mm (6.0 inches). Two rectilinear vertical sides 113 64 mm (2.5 inches) tall×508 mm (20 inches) in length are affixed to the long edges of the base 112 to form a U-shaped trough 111 having a length of 508 mm (20.0 inches), an internal width of 152 mm (6.0 inches), and an internal depth of 51 mm (2.0 inches). The front and back ends of the trough 111 are not enclosed.

A slab of open-cell polyurethane foam 114 with dimensions 508×152×25 mm is wrapped in polyethylene film and placed in the bottom of the trough 111 in such a way that the edges of the foam 114 and the trough 111 are aligned, and the upper surface of the polyethylene film is smooth and free of seams, wrinkles or imperfections. The polyurethane foam 114 has a compressive modulus of 0.48 psi. A reference line is drawn across the width of the upper surface of the polyethylene cover 152 mm (6.0 inches) from one end (the front edge) parallel to the transverse centerline using an indelible marker.

A rectilinear polycarbonate top plate 115 has a nominal thickness of 12.5 mm (0.5 inch), a length of 508 mm (20.0 inches), and a width of 146 mm (5.75 inches). A 51 mm (2.0 inch) diameter hole is bored in the center of the top plate 115 (i.e. the center of the hole is located at the intersection of the longitudinal and transverse axes of the upper surface of the top plate 115). A polycarbonate cylinder 116 with an outside diameter of 51 mm (2.0 inches), an internal diameter of 37.5 mm (1.5 inches) and a height of 102 mm (4.0 inches) is glued into the hole in the top plate 115 so that the bottom edge of the cylinder 116 is flush with the lower surface of the top plate 115 and the cylinder 116 protrudes vertically 89 mm (3.5 inches) above the upper surface of the top plate 115, and the seam between the cylinder 116 and the top plate 115 is water-tight. An annular recess 117 with a height of 2 mm and a diameter of 44.5 mm (1.75 inches) is machined into the bottom internal edge of the cylinder 116. Two 1 mm diameter holes are drilled at a 45° angle to the upper surface of the top plate 115 so that the holes intersect the inner surface of the cylinder 116 immediately above the recess 117 and are at opposite sides of the cylinder 116 (i.e. 180° apart). Two stainless steel wires 118 having a diameter of 1 mm are glued into the holes in a watertight fashion so that one end of each wire is flush with the inner cylinder wall and the other end protrudes from the upper surface of the top plate 115. These wires are referred to as electrodes herein below. A reference line is scribed across the width of the top plate 115 152 mm (6.0 inches) from the front edge parallel to the transverse centerline. The top plate 1415/cylinder 116 assembly has a weight of approximately 1180 grams.

Two steel weights each weighing 0.9 Kg and measuring 127 mm (5 inches) wide, 50 mm (1.97 inches) deep, and approximately 16 mm (0.63 inches tall) are also required.

Procedure

All testing is carried out at 23±2° C. and 35±15% relative humidity.

The polycarbonate trough 111 containing the wrapped foam slab 114 is placed on a suitable flat horizontal surface. A disposable absorbent product is removed from its packaging and the cuff elastics are cut at suitable intervals to allow the product to lay flat. The product is weighed to within ±0.1 grams on a suitable top-loading balance then placed on the covered foam slab 114 in the acquisition apparatus with the front waist edge of the product aligned with the reference mark on the polyethylene cover. The product is centered along the longitudinal centerline of the apparatus with the topsheet (body-side) of the product facing upwards and the rear waist edge toward the rear end of the foam slab 114. The top plate 115 is placed on top of the product with the protruding cylinder facing upwards. The scribed reference line is aligned with the front waist edge of the product and the rear end of the top plate 115 is aligned with the rear edge of the foam slab 114. The two 0.9 Kg weights are then gently placed onto the top plate 115 so that the width of each weight is parallel to the transverse centerline of the top plate, and each weight is 83 mm (3.25 inches) from the front or rear edge of the top plate 115.

A suitable electrical circuit is connected to the two electrodes to detect the presence of an electrically conductive fluid between them.

A suitable pump; e.g. Model 7520-00 supplied by Cole Parmer Instruments, Chicago, USA, or equivalent; is set up to discharge a 0.9 mass % aqueous solution of sodium chloride through a flexible plastic tube having an internal diameter of 4.8 mm (3/16 inch), e.g. Tygon® R-3603 or equivalent. The 0.9% NaCl solution is stained with Indigo carmine ($C_{16}H_8N_2Na_2O_8S_2$) by Merck (104724 Indigocarmin C.I. 73015), using 40 mg per liter of 0.9% NaCl solution. The end portion of the tube is clamped vertically so that it is centered within the cylinder 116 attached to the top plate 115 with the discharge end of the tube facing downwards and located 50 mm (2 inches) below the upper edge of the cylinder 116. The pump is operated via a timer and is pre-calibrated to discharge a gush of 90.0 ml of the 0.9% saline solution at a rate of 15 ml/sec.

The pump is activated and a timer started immediately upon activation. The pump delivers 90 mL of 0.9% NaCl solution to the cylinder 116 at a rate of 15 ml/sec, then stops. As test fluid is introduced to the cylinder 116, it typically builds up on top of the absorbent structure to some extent. This fluid completes an electrical circuit between the two electrodes in the cylinder. After the gush has been delivered, the meniscus of the solution drops as the fluid is absorbed into the structure. When the electrical circuit is broken due to the absence of free fluid between the electrodes in the cylinder, the time is noted.

The acquisition time for a particular gush is the time interval between activation of the pump for that gush, and the point at which the electrical circuit is broken.

Four gushes are delivered to the product in this fashion; each gush is 90 ml and is delivered at 15 ml/sec. The time interval between the beginnings of each gush is 300 seconds.

Apparatus Imaging System (for Optional Use in Sample Preparation and Setups Step 10)

Image Acquisition Hardware

The image acquisition hardware consists of a computer, and lighting rigs 213 that contains a digital camera 211, such as a Fuji HC2500 (211) or Sony DFW-X700 (211). The color calibration chart is a standard 8.5"×11" Gretag-Macbeth color chart, and two lights 212.

Connecting the Peripherals

The Fuji HC2500 camera has a PCI interface card that is installed in PCI slot 2 of the computer. The Sony DFW-X700 plugs into any Firewire (IEEE-1348) port of the computer.

Lighting Rig

Figure 7:
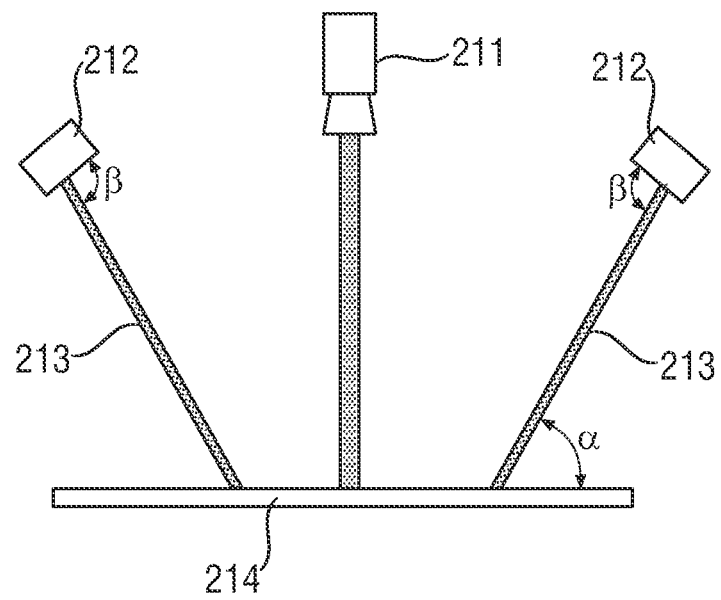
FIG. 7 is a schematic drawing of an apparatus imaging system graphic for conducting the test method to visualize backsheet see-through in accordance with an embodiment of the present disclosure.

The lighting rig 213 is shown in FIG. 7. The light 212 should fulfill the requirements of D65 such as an OSRAM OSDULUXL36W12 or equivalent (CC temperature/Kelvin 5400K; color daylight; CRI 90CRI). The angle α between the base 214 and the lighting rig 213 is 70°. The angle β between the lighting rig 213 and the light 212 should be adjusted to achieve even illumination of base 214.

Sample Preparation and Setup

1. Directly after all liquid is absorbed by the diaper the diaper must be removed from the test apparatus.
2. Immediately open the product with topsheet facing upwardly.
3. Unfold the diaper and tear off the elastics from the diaper along the continuous bond.
4. Lay the diaper flat and rectangular with the topsheet facing downwardly onto the table surface without any folds.
5. Use one hand to hold the front waist edge of the diaper down onto the table surface to avoid any movement.
6. Gently place the weight 312 (9 Kg and measuring 148 mm (5.83 inches) wide, 38 mm (1.5 inches) deep, and approximately 101 mm (3.98 inches tall)) at the front waist edge of the diaper in an angle of 45° or less onto the baby diaper front waist edge next to your hand. The side of the weight 312 should be parallel to the transverse axis of the diaper. Now slide the weight towards the back waist edge of the diaper, by keeping the angle of 45° or lower such that the weight is sliding over the diaper with only one of its edges 313, by gripping the weight with handle 311. This should take approximately 1 to 2 sec for a diaper having a longitudinal extension of 400 mm to 500 mm.
7. Take the front and waist edges of the diaper, lift them up and fold the diaper in a way that it builds a circle. During that procedure the crotch region of the diaper should still be in contact with the table.
8. Release the diaper ends and lay down the diaper flat and rectangular with the topsheet facing downwardly onto the table surface without any folds.
9. Slightly touch the back-sheet surface with your flat hand and move your hands three times gently in cross direction (i.e. parallel to the transverse axis of the diaper) back and forth.
10. Visually inspect with the naked eye the diaper: Areas, where the backsheet closely sticks to the absorbent core can be recognized as darker areas where the stained absorbent core shines through the backsheet to a certain extent. Areas where the backsheet has separated from the absorbent core can be identified by lighter colors. The difference between a backsheet with large areas being adhesively attached to the core and a backsheet with only small areas being adhesively attached to the core is typically readily apparent.

To archive the result, the diapers can be photographed using the equipment described under "Apparatus imaging system".

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable diaper comprising a backsheet, a topsheet and therein between an absorbent core, the absorbent core having a longitudinal direction with a longitudinal axis and perpendicular thereto a lateral direction with a transverse axis, the absorbent core comprising a front region, a back region and a crotch region therein between and a front lateral edge, an opposing back lateral edge, and longitudinally extending side edges, wherein the absorbent core comprises superabsorbent polymer particles, the superabsorbent polymer particles being immobilized by a first core adhesive, wherein the absorbent core comprises less than 5% of airfelt, and wherein
   a) the absorbent core is attached to the backsheet of the disposable diaper in attachment zones adjacent to the front lateral edge and the back lateral edge of the absorbent core; and
   b) the absorbent core is attached to the backsheet of the disposable diaper in the crotch region of the absorbent core in attachment zones adjacent to the longitudinal side edges of the absorbent core;
wherein the absorbent core comprises one or more channels which are free of the superabsorbent polymer particles; wherein the one or more channels do not extend onto the front and back lateral edges and longitudinal edges of the absorbent core.

2. The disposable diaper of claim 1, wherein the backsheet comprises a film and one or more nonwoven webs, wherein the basis weight of the backsheet including the film and the one or more nonwoven webs is less than 70 g/m$^2$, and wherein the film has a basis weight of less than 25 g/m$^2$.

3. The disposable diaper of claim 1, wherein the backsheet is non-elastic.

4. The disposable diaper of claim 1, wherein the backsheet is highly non-elastic.

5. The disposable diaper of claim 1, wherein the absorbent core is attached to the topsheet at least in the front region and in the crotch region of the absorbent core.

6. The disposable diaper of claim 1, wherein absorbent material of the absorbent core comprises more than 95% of the superabsorbent polymer particles.

7. The disposable diaper of claim 1, wherein the absorbent core comprises first and second carrier substrates, and wherein the superabsorbent polymer particles are provided between the first and second carrier substrates.

8. The disposable diaper of claim 1, wherein the first core adhesive is a hot melt adhesive.

9. The disposable diaper of claim 1, wherein the one or more channels are provided in areas other than the attachment zones.

10. The disposable diaper of claim 1, wherein the absorbent core is attached to the backsheet by an adhesive.

11. The disposable diaper of claim 10, wherein the adhesive is a hot melt adhesive.

12. The disposable diaper of claim 1, wherein the absorbent core is unattached to the backsheet in any other region.

13. The disposable diaper of claim 1, wherein the absorbent core is not attached to the backsheet over the entire absorbent core surface.

14. The disposable diaper of claim 1, wherein the absorbent core is attached to the backsheet of the disposable diaper in the crotch region of the absorbent core in one or more than one attachment zones on or adjacent to the longitudinal axis of the absorbent core, wherein the one or more than one attachment zones cover from 0.2% to 3% of the total surface area of the absorbent core.

15. The disposable diaper of claim 14, wherein the disposable diaper comprises a wetness indicator, and wherein the wetness indicator is placed between the absorbent core and the backsheet in at least one of the one or more attachment zones.

16. A disposable diaper comprising a backsheet, a topsheet and therein between an absorbent core, the absorbent core having a longitudinal direction with a longitudinal axis and perpendicular thereto a lateral direction with a transverse axis, the absorbent core comprising a front region, a back region and a crotch region therein between and a front lateral edge, an opposing back lateral edge, and longitudinally extending side edges, wherein the absorbent core comprises superabsorbent polymer particles, the superabsorbent polymer particles being immobilized by a first core adhesive, wherein the absorbent core comprises less than 5% of airfelt, and wherein
   a) the absorbent core is attached to the backsheet of the disposable diaper in attachment zones adjacent to the front lateral edge and the back lateral edge of the absorbent core; and
   b) the absorbent core is attached to the backsheet of the disposable diaper in the crotch region of the absorbent core in attachment zones adjacent to the longitudinal side edges of the absorbent core;
wherein the absorbent core comprises one or more channels which are free of the superabsorbent polymer particles; wherein the one or more channels are provided in areas other than the attachment zones; wherein the one or more channels do not extend onto the front and back lateral edges and longitudinal edges of the absorbent core.

17. A disposable diaper comprising a backsheet, a topsheet and therein between an absorbent core, the absorbent core having a longitudinal direction with a longitudinal axis and perpendicular thereto a lateral direction with a transverse axis, the absorbent core comprising a front region, a back region and a crotch region therein between and a front lateral edge, an opposing back lateral edge, and longitudinally extending side edges, wherein the absorbent core comprises superabsorbent polymer particles, the superabsorbent polymer particles being immobilized by a first core adhesive, wherein the absorbent core comprises less than 5% of airfelt, and wherein
  a) the absorbent core is attached to the backsheet of the disposable diaper in attachment zones adjacent to the front lateral edge and the back lateral edge of the absorbent core;
  b) the absorbent core is attached to the backsheet of the disposable diaper in the crotch region of the absorbent core in attachment zones adjacent to the longitudinal side edges of the absorbent core; and
  c) the absorbent core is attached to the backsheet of the disposable diaper in the crotch region of the absorbent core through a wetness indicator;

wherein the absorbent core comprises one or more channels which are free of the superabsorbent polymer particles; wherein the one or more channels are provided in areas other than the attachment zones; wherein the one or more channels do not extend onto the front and back lateral edges and longitudinal edges of the absorbent core.

* * * * *